(12) United States Patent
Fujita et al.

(10) Patent No.: US 8,530,649 B2
(45) Date of Patent: Sep. 10, 2013

(54) POLYMER COMPLEX

(75) Inventors: Makoto Fujita, Chiba (JP); Masaki Kawano, Chiba (JP); Takehide Chou, Koube (JP); Takahiro Kojima, Tokyo-to (JP)

(73) Assignees: The University of Tokyo, Tokyo (JP); Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 797 days.

(21) Appl. No.: 12/224,805

(22) PCT Filed: Mar. 2, 2007

(86) PCT No.: PCT/JP2007/054600
§ 371 (c)(1),
(2), (4) Date: Sep. 5, 2008

(87) PCT Pub. No.: WO2007/102594
PCT Pub. Date: Sep. 13, 2007

(65) Prior Publication Data
US 2011/0098414 A1    Apr. 28, 2011

(30) Foreign Application Priority Data
Mar. 8, 2006    (JP) .................................. 2006-063416

(51) Int. Cl.
*C07F 9/80* (2006.01)
(52) U.S. Cl.
USPC ........................... 544/181; 524/413; 524/612
(58) Field of Classification Search
USPC .................... 524/612, 413; 544/181
See application file for complete search history.

(56) References Cited

U.S. PATENT DOCUMENTS

| 5,019,263 A | 5/1991 | Haag et al. | |
|---|---|---|---|
| 5,648,508 A * | 7/1997 | Yaghi | 556/9 |
| 2003/0004364 A1* | 1/2003 | Yaghi et al. | 556/46 |
| 2010/0324249 A1* | 12/2010 | Fujita et al. | 528/9 |

FOREIGN PATENT DOCUMENTS

| JP | 7-185275 | 7/1995 |
|---|---|---|
| JP | 8-318141 | 12/1996 |
| JP | 2001-232156 | 8/2001 |
| JP | 2003-55271 | 2/2003 |
| JP | 2003-210950 | 7/2003 |
| JP | 2005-255545 | 9/2005 |
| JP | 2006-188560 | 7/2006 |

OTHER PUBLICATIONS

Ohmori et. al. CrystEngComm, 2005, 7(40), 255-259 published on web on Mar. 30, 2005.*
Ohmori et. al. "A Two-in-One Crystal . . . " Angew. Chem. Int. Ed. 2005, 44, 1962-1964, published online on Feb. 21, 2005.*
Kawano et al. JACS 2007, 129, 15418-15419, published on web Nov. 22, 2007.*
O. Ohmori et al., "Crystal-to-Crystal Guest Exchange of Large Organic Molecules within a 3D Coordination Network," J. Am. Chem. Soc., vol. 126, No. 50, pp. 16292-16293 (2004).
U.S. Appl. No. 12/449,925 (now issued Patent No, 8,236,867) Notice of Allowance dated Apr. 9, 2012.
U.S. Appl. No. 12/449,925 (now issued Patent No, 8,236,867) Supplemental Notice of Allowability dated May 25, 2012.

* cited by examiner

*Primary Examiner* — Ling Choi
*Assistant Examiner* — Wenwen Cai
(74) *Attorney, Agent, or Firm* — Finnegan, Henderson, Farabow, Garrett & Dunner, LLP

(57) ABSTRACT

A polymer complex having two or more kinds of channel groups through which specific compounds ranging from gaseous small molecules to large molecules such as proteins and other biomolecules can be selectively incorporated and/or released and/or transported is provided. The polymer complex includes an aromatic compound ligand, a central metal ion, and an uncoordinating aromatic compound. In the polymer complex, the uncoordinating aromatic compound is intercalated between aromatic compound ligands in a three-dimensional coordination network. Each of two or more kinds of channel groups contains channels identical with one another and having inherent affinity for guest components. The uncoordinating aromatic compound has a specific substituent A at a specific position on the aromatic ring thereof, and the uncoordinating aromatic compound is arranged regularly such that the substituent A is directed to the inside of a specific channel group B out of the two or more kinds of channel groups.

16 Claims, 37 Drawing Sheets

FIG.2
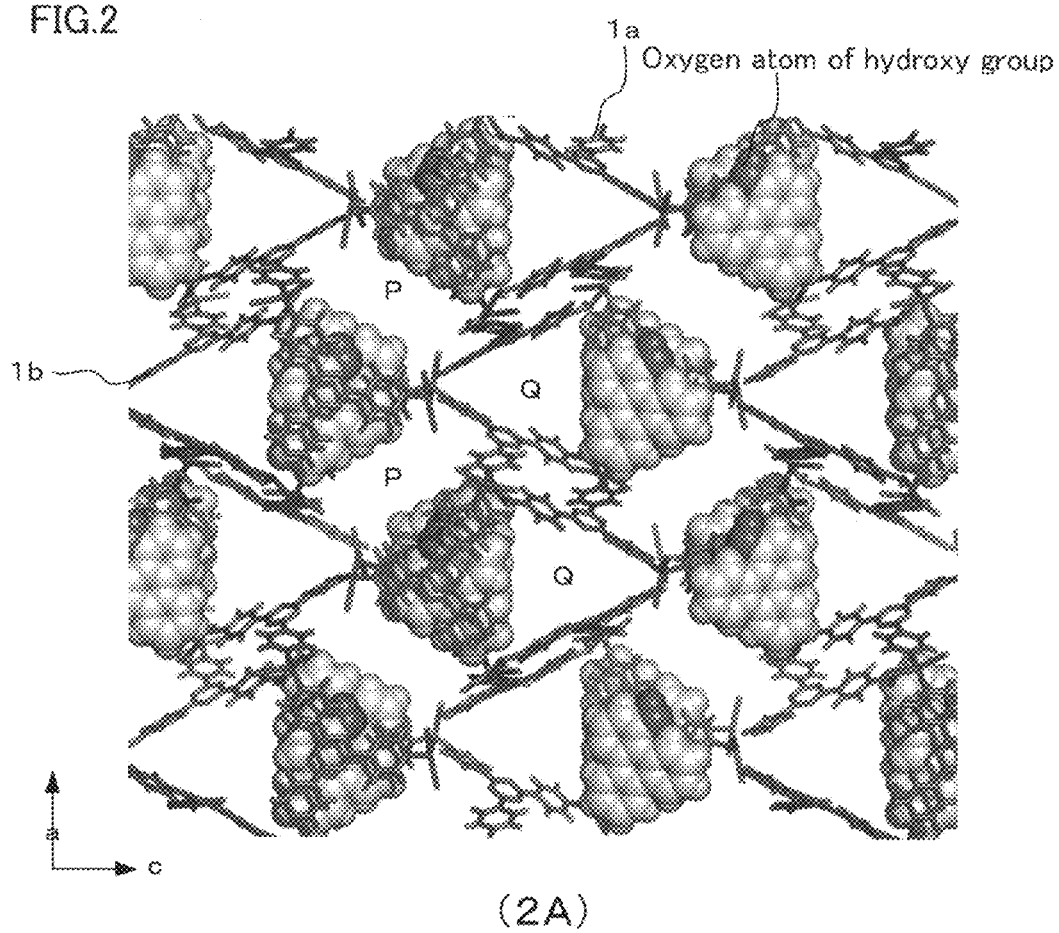
(2A)
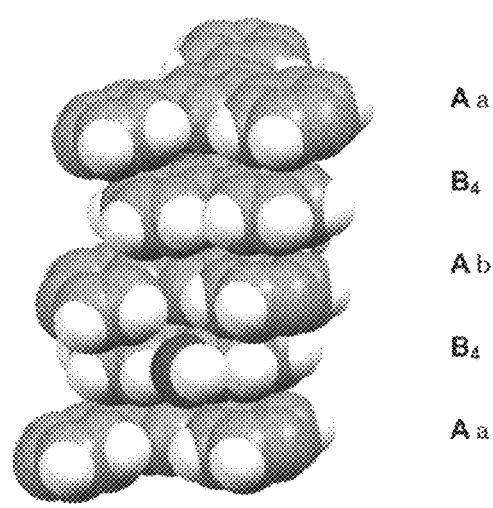
(2B)

FIG.3
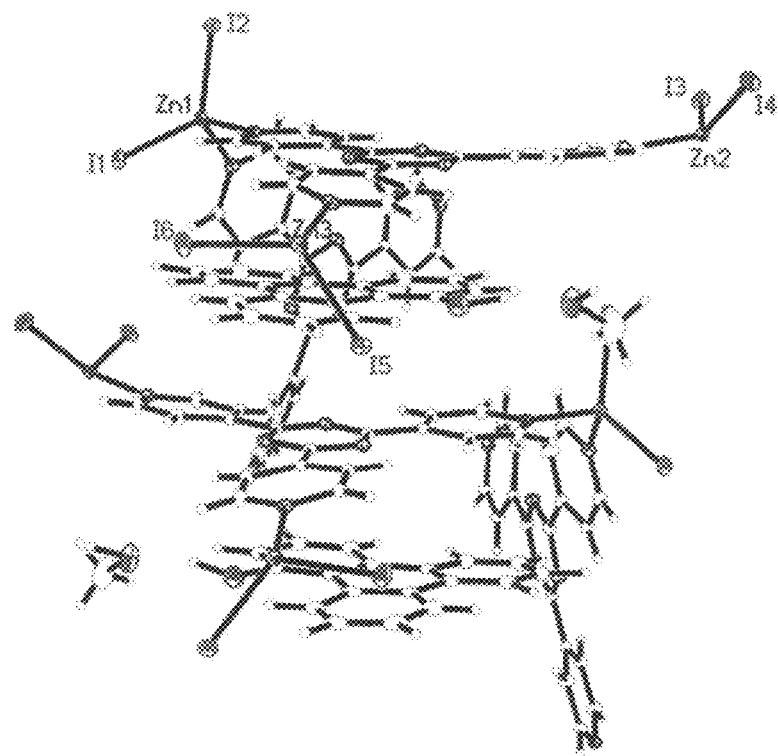
(3A)
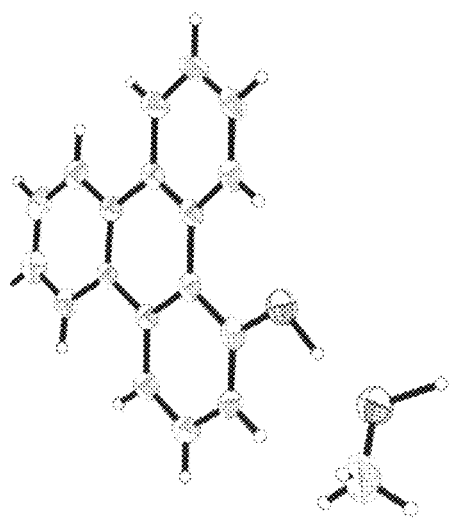
(3B)

FIG.4
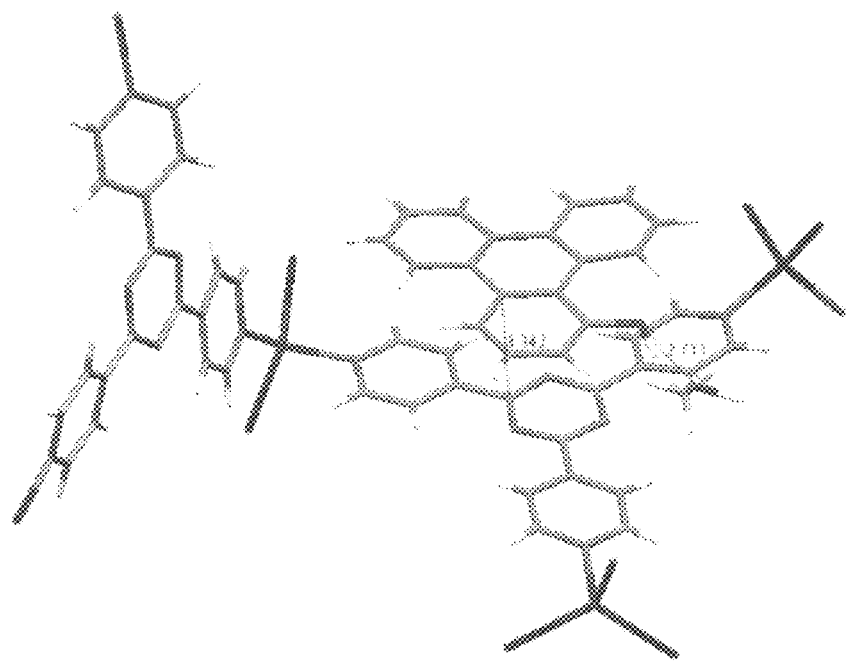
(4A)
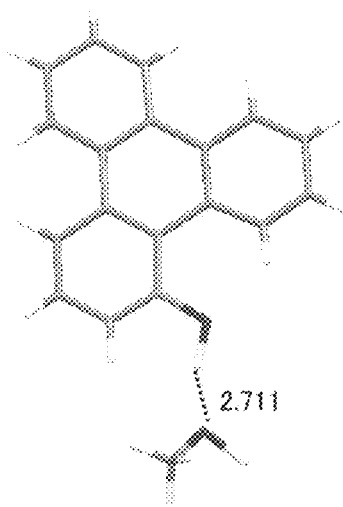
(4B)

Crystal plane X

Crystal plane Y
apart by 1 unit cell
from crystal plane X

FIG.7
(a)
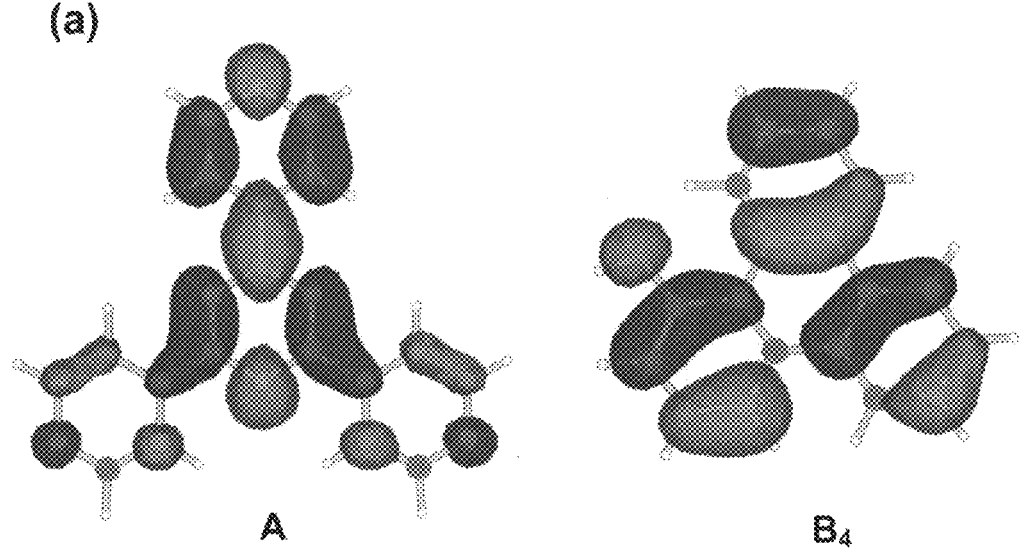
A    B₄
(b)
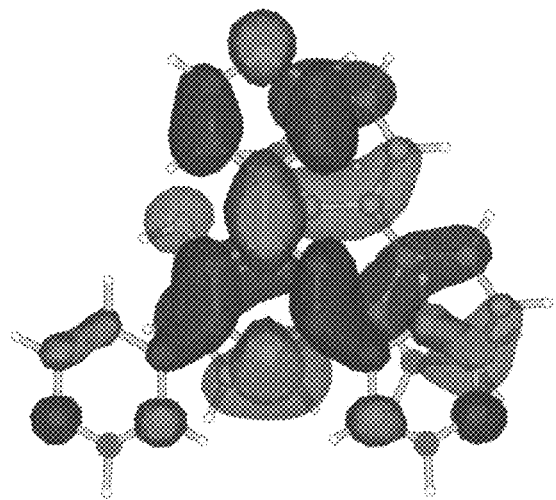

FIG.8
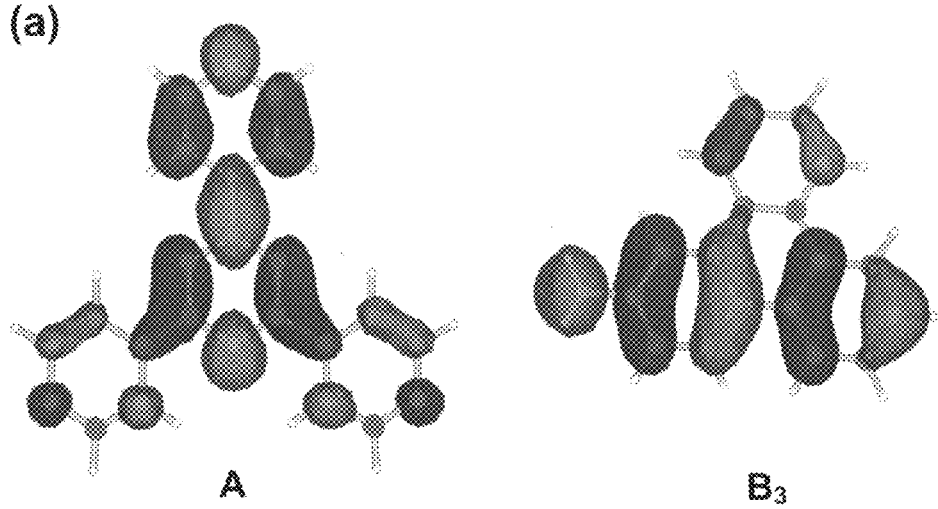
A          B₃
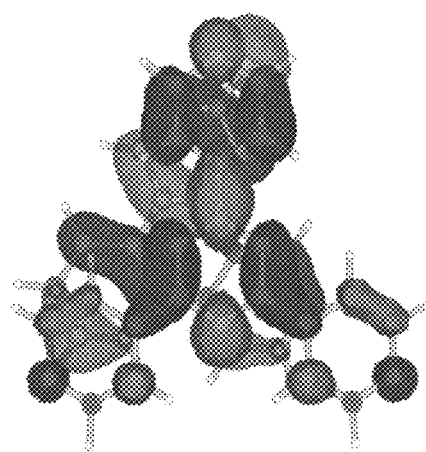

FIG.9

(Table 2)   Crystal data and structure refinement for pbca.

| | |
|---|---|
| Identification code | pbca |
| Empirical formula | C79 H60 I6 N16 O10 Zn3 |
| Formula weight | 2350.94 |
| Temperature | 90(2) K |
| Wavelength | 0.71073 Å |
| Crystal system | Orthorhombic |
| Space group | Pbca |
| Unit cell dimensions | a = 27.123(4) Å    α= 90°. |
| | b = 13.6817(18) Å    β= 90°. |
| | c = 45.995(6) Å    γ = 90°. |
| Volume | 17068(4) Å$^3$ |
| Z | 8 |
| Density (calculated) | 1.830 Mg/m$^3$ |
| Absorption coefficient | 3.072 mm$^{-1}$ |
| F(000) | 9072 |
| Crystal size | 0.45 x 0.10 x 0.05 mm$^3$ |
| Theta range for data collection | 1.72 to 30.08°. |
| Index ranges | -38<=h<=37, -19<=k<=18, -64<=l<=63 |
| Reflections collected | 248570 |
| Independent reflections | 24916 [R(int) = 0.1047] |
| Completeness to theta = 30.08° | 99.4 % |
| Absorption correction | None |
| Max. and min. transmission | 0.8615 and 0.3386 |
| Refinement method | Full-matrix least-squares on F$^2$ |
| Data / restraints / parameters | 24916 / 36 / 1117 |
| Goodness-of-fit on F$^2$ | 1.030 |
| Final R indices [I>2sigma(I)] | R1 = 0.0382, wR2 = 0.0742 |
| R indices (all data) | R1 = 0.0811, wR2 = 0.0867 |
| Largest diff. peak and hole | 0.935 and -0.598 e.Å$^{-3}$ |

FIG.10

(Table 3)  Atomic coordinates ( x 10⁴) and equivalent isotropic displacement parameters ($Å^2 \times 10^3$) for pbca.  U(eq) is defined as one third of the trace of the orthogonalized $U^{ij}$ tensor.

(Table 3 − 1)

|        | x        | y         | z        | U(eq)  |
|--------|----------|-----------|----------|--------|
| Zn(1)  | 482(1)   | 11407(1)  | 704(1)   | 18(1)  |
| Zn(2)  | 5333(1)  | 11457(1)  | 937(1)   | 20(1)  |
| Zn(3)  | 2509(1)  | 8440(1)   | 3110(1)  | 19(1)  |
| I(1)   | -187(1)  | 10458(1)  | 969(1)   | 28(1)  |
| I(2)   | 477(1)   | 13243(1)  | 611(1)   | 30(1)  |
| I(3)   | 5215(1)  | 12323(1)  | 451(1)   | 33(1)  |
| I(4)   | 5788(1)  | 12246(1)  | 1358(1)  | 39(1)  |
| I(5)   | 3041(1)  | 6915(1)   | 3038(1)  | 28(1)  |
| I(6)   | 1589(1)  | 8315(1)   | 3217(1)  | 31(1)  |
| C(1)   | 1936(1)  | 11239(3)  | -1344(1) | 23(1)  |
| C(2)   | 1724(1)  | 10745(3)  | -1116(1) | 24(1)  |
| C(3)   | 2139(2)  | 9794(3)   | -1573(1) | 27(1)  |
| C(4)   | 1932(1)  | 9252(3)   | -1352(1) | 22(1)  |
| C(5)   | 1722(1)  | 9731(3)   | -1117(1) | 19(1)  |
| C(6)   | 1491(1)  | 9177(3)   | -877(1)  | 19(1)  |
| C(7)   | 713(1)   | 5512(3)   | -1079(1) | 23(1)  |
| C(8)   | 886(1)   | 6450(3)   | -1038(1) | 23(1)  |
| C(9)   | 737(1)   | 5209(3)   | -587(1)  | 22(1)  |
| C(10)  | 904(2)   | 6143(3)   | -530(1)  | 24(1)  |
| C(11)  | 982(1)   | 6780(3)   | -759(1)  | 19(1)  |
| C(12)  | 1144(1)  | 7797(3)   | -709(1)  | 20(1)  |
| C(13)  | 516(1)   | 9770(3)   | 272(1)   | 21(1)  |
| C(14)  | 672(1)   | 9240(3)   | 35(1)    | 21(1)  |
| C(15)  | 946(2)   | 11131(3)  | 122(1)   | 24(1)  |
| C(16)  | 1125(2)  | 10647(3)  | -122(1)  | 28(1)  |
| C(17)  | 989(1)   | 9683(3)   | -165(1)  | 19(1)  |
| C(18)  | 1156(1)  | 9143(3)   | -429(1)  | 20(1)  |
| C(21)  | 1090(1)  | 10830(3)  | 1218(1)  | 20(1)  |

FIG.11

(Table 3 − 2)

|        | x       | y        | z       | U(eq) |
|--------|---------|----------|---------|-------|
| C(22)  | 1501(1) | 10683(3) | 1386(1) | 19(1) |
| C(23)  | 1567(1) | 11226(3) | 820(1)  | 21(1) |
| C(24)  | 1995(1) | 11075(3) | 974(1)  | 20(1) |
| C(25)  | 1968(1) | 10801(2) | 1265(1) | 16(1) |
| C(26)  | 2415(1) | 10644(2) | 1441(1) | 16(1) |
| C(27)  | 4254(1) | 11063(3) | 944(1)  | 22(1) |
| C(28)  | 3788(1) | 10907(3) | 1054(1) | 21(1) |
| C(29)  | 4606(1) | 10862(3) | 1394(1) | 26(1) |
| C(30)  | 4157(1) | 10693(3) | 1521(1) | 24(1) |
| C(31)  | 3734(1) | 10730(2) | 1350(1) | 17(1) |
| C(32)  | 3240(1) | 10609(2) | 1481(1) | 16(1) |
| C(33)  | 3046(1) | 9333(3)  | 2619(1) | 24(1) |
| C(34)  | 3119(1) | 9680(3)  | 2339(1) | 22(1) |
| C(35)  | 2209(1) | 9583(3)  | 2588(1) | 20(1) |
| C(36)  | 2251(1) | 9932(3)  | 2308(1) | 19(1) |
| C(37)  | 2712(1) | 9967(2)  | 2178(1) | 16(1) |
| C(38)  | 2766(1) | 10268(2) | 1871(1) | 16(1) |
| N(1)   | 2146(1) | 10777(2) | -1571(1)| 21(1) |
| N(2)   | 636(1)  | 4900(2)  | -856(1) | 19(1) |
| N(3)   | 651(1)  | 10702(2) | 319(1)  | 19(1) |
| N(4)   | 1370(1) | 8248(2)  | -929(1) | 21(1) |
| N(5)   | 1034(1) | 8200(2)  | -451(1) | 20(1) |
| N(6)   | 1395(1) | 9664(2)  | -630(1) | 20(1) |
| N(21)  | 1117(1) | 11110(2) | 939(1)  | 17(1) |
| N(22)  | 4658(1) | 11061(2) | 1111(1) | 20(1) |
| N(23)  | 2596(1) | 9265(2)  | 2740(1) | 18(1) |
| N(24)  | 2851(1) | 10758(2) | 1310(1) | 17(1) |
| N(25)  | 3220(1) | 10361(2) | 1766(1) | 17(1) |
| N(26)  | 2349(1) | 10407(2) | 1720(1) | 17(1) |
| C(101) | 2628(2) | 8081(3)  | 1503(1) | 26(1) |
| C(102) | 3158(2) | 8128(3)  | 1498(1) | 30(1) |
| C(103) | 3410(2) | 8349(3)  | 1249(1) | 30(1) |
| C(104) | 3163(2) | 8556(3)  | 993(1)  | 32(1) |

FIG.12

(Table 3 − 3)

|        | x        | y         | z       | U(eq)  |
|--------|----------|-----------|---------|--------|
| C(105) | 2653(2)  | 8532(3)   | 989(1)  | 31(1)  |
| C(106) | 2380(2)  | 8300(3)   | 1238(1) | 24(1)  |
| C(107) | 1840(2)  | 8295(3)   | 1229(1) | 25(1)  |
| C(108) | 1585(2)  | 8466(3)   | 965(1)  | 33(1)  |
| C(109) | 1080(2)  | 8508(3)   | 956(1)  | 38(1)  |
| C(110) | 807(2)   | 8376(3)   | 1209(1) | 39(1)  |
| C(111) | 1042(2)  | 8198(3)   | 1465(1) | 32(1)  |
| C(112) | 1564(2)  | 8142(3)   | 1482(1) | 26(1)  |
| C(113) | 1820(2)  | 7913(3)   | 1754(1) | 27(1)  |
| C(114) | 1541(2)  | 7707(3)   | 2009(1) | 34(1)  |
| C(115) | 1766(2)  | 7441(3)   | 2265(1) | 37(1)  |
| C(116) | 2278(2)  | 7360(3)   | 2273(1) | 35(1)  |
| C(117) | 2556(2)  | 7551(3)   | 2032(1) | 31(1)  |
| C(118) | 2341(2)  | 7850(3)   | 1766(1) | 27(1)  |
| O(101) | 3423(1)  | 7943(2)   | 1748(1) | 39(1)  |
| C(201) | 2230(4)  | −366(10)  | 4336(3) | 45(2)  |
| C(202) | 2280(4)  | 342(11)   | 4534(3) | 64(3)  |
| C(203) | 2110(5)  | 1247(10)  | 4453(3) | 84(4)  |
| C(204) | 1890(7)  | 1399(13)  | 4191(4) | 76(5)  |
| C(205) | 1851(7)  | 691(12)   | 3993(5) | 60(5)  |
| C(206) | 2008(6)  | −219(13)  | 4060(4) | 57(4)  |
| N(201) | 2388(2)  | −1350(6)  | 4409(2) | 65(2)  |
| O(201) | 2648(6)  | −1446(15) | 4631(3) | 90(5)  |
| O(202) | 2277(3)  | −2007(6)  | 4242(2) | 112(3) |
| C(211) | 2382(7)  | −123(17)  | 4442(5) | 36(5)  |
| C(212) | 2249(7)  | 776(19)   | 4409(5) | 38(4)  |
| C(213) | 1980(12) | 1040(20)  | 4137(9) | 49(7)  |
| C(214) | 1854(13) | 270(30)   | 3957(9) | 46(8)  |
| C(215) | 2019(13) | −600(30)  | 4000(8) | 45(7)  |
| C(216) | 2254(6)  | −834(17)  | 4240(4) | 36(5)  |
| N(211) | 2693(4)  | −425(10)  | 4698(3) | 34(3)  |
| O(211) | 2832(4)  | 210(8)    | 4858(2) | 40(3)  |
| O(212) | 2764(11) | −1340(20) | 4731(6) | 54(7)  |

FIG.13

(Table 3 — 4)

|        | x       | y       | z       | U(eq)  |
|--------|---------|---------|---------|--------|
| C(221) | 2967(2) | 1761(5) | 250(1)  | 55(2)  |
| C(222) | 2836(2) | 811(5)  | 275(1)  | 61(2)  |
| C(223) | 3194(3) | 123(5)  | 277(1)  | 69(2)  |
| C(224) | 3686(3) | 396(6)  | 253(1)  | 73(2)  |
| C(225) | 3808(2) | 1375(6) | 228(1)  | 60(2)  |
| C(226) | 3443(2) | 2056(4) | 224(1)  | 54(2)  |
| N(221) | 2568(3) | 2549(6) | 247(1)  | 90(2)  |
| O(221) | 2159(3) | 2268(7) | 278(1)  | 154(4) |
| O(222) | 2717(4) | 3380(5) | 204(2)  | 145(3) |
| C(231) | 5606(2) | -59(4)  | 2337(1) | 42(1)  |
| C(232) | 5623(2) | -496(4) | 2609(1) | 49(1)  |
| C(233) | 5794(2) | 53(4)   | 2837(1) | 54(1)  |
| C(234) | 5937(2) | 1005(4) | 2797(1) | 54(1)  |
| C(235) | 5925(2) | 1419(4) | 2524(1) | 60(2)  |
| C(236) | 5758(2) | 877(4)  | 2286(1) | 51(1)  |
| N(231) | 5393(2) | -618(3) | 2092(1) | 49(1)  |
| O(231) | 5191(2) | -1419(3)| 2150(1) | 65(1)  |
| O(232) | 5412(2) | -257(3) | 1848(1) | 59(1)  |
| C(241) | 4366(2) | 559(4)  | 2697(1) | 37(1)  |
| C(242) | 4380(2) | -439(4) | 2729(1) | 44(1)  |
| C(243) | 4324(2) | -824(4) | 3007(1) | 46(1)  |
| C(244) | 4250(2) | -215(4) | 3241(1) | 44(1)  |
| C(245) | 4233(2) | 780(4)  | 3203(1) | 52(1)  |
| C(246) | 4292(2) | 1188(4) | 2928(1) | 48(1)  |
| N(241) | 4433(2) | 967(4)  | 2406(1) | 49(1)  |
| O(241) | 4458(2) | 379(4)  | 2200(1) | 68(1)  |
| O(242) | 4466(2) | 1858(3) | 2381(1) | 69(1)  |
| C(301) | 4751(2) | 7790(6) | 1517(2) | 80(2)  |
| O(301) | 4417(1) | 8123(3) | 1725(1) | 57(1)  |

FIG.14

(Table 4) Anisotropic displacement parameters ($Å^2 \times 10^3$) for pbca. The anisotropic displacement factor exponent takes the form: $-2\pi^2[h^2a^{*2}U^{11} + ... + 2hk\,a^*b^*U^{12}]$ (Table 4 — 1)

|   | $U^{11}$ | $U^{22}$ | $U^{33}$ | $U^{23}$ | $U^{13}$ | $U^{12}$ |
|---|---|---|---|---|---|---|
| Zn(1) | 18(1) | 21(1) | 16(1) | -1(1) | 0(1) | 2(1) |
| Zn(2) | 18(1) | 17(1) | 25(1) | 0(1) | 2(1) | 2(1) |
| Zn(3) | 23(1) | 20(1) | 14(1) | 2(1) | -2(1) | -3(1) |
| I(1) | 20(1) | 38(1) | 27(1) | 4(1) | 2(1) | 0(1) |
| I(2) | 32(1) | 21(1) | 36(1) | 1(1) | 2(1) | 6(1) |
| I(3) | 33(1) | 30(1) | 36(1) | 16(1) | 8(1) | 7(1) |
| I(4) | 36(1) | 38(1) | 44(1) | -14(1) | -6(1) | -10(1) |
| I(5) | 33(1) | 21(1) | 29(1) | -1(1) | -3(1) | 1(1) |
| I(6) | 24(1) | 44(1) | 26(1) | 11(1) | 2(1) | -5(1) |
| C(1) | 30(2) | 18(2) | 21(2) | -2(1) | 7(2) | 0(2) |
| C(2) | 32(2) | 19(2) | 21(2) | -5(1) | 11(2) | 1(2) |
| C(3) | 37(2) | 21(2) | 22(2) | -7(2) | 10(2) | 0(2) |
| C(4) | 28(2) | 16(2) | 24(2) | -3(1) | 6(2) | -2(1) |
| C(5) | 19(2) | 19(2) | 19(2) | 0(1) | 1(1) | 0(1) |
| C(6) | 21(2) | 19(2) | 17(2) | -1(1) | 0(1) | -2(1) |
| C(7) | 29(2) | 21(2) | 19(2) | -2(1) | -1(2) | -7(2) |
| C(8) | 30(2) | 20(2) | 18(2) | 3(1) | 0(2) | -4(2) |
| C(9) | 27(2) | 20(2) | 20(2) | 3(1) | -2(2) | -3(2) |
| C(10) | 36(2) | 20(2) | 16(2) | 0(1) | -4(2) | -3(2) |
| C(11) | 16(2) | 18(2) | 23(2) | -2(1) | 0(1) | -1(1) |
| C(12) | 21(2) | 18(2) | 20(2) | -2(1) | -1(1) | 1(1) |
| C(13) | 23(2) | 24(2) | 17(2) | 2(1) | 2(2) | 0(2) |
| C(14) | 23(2) | 18(2) | 23(2) | 0(1) | 0(2) | -3(1) |
| C(15) | 34(2) | 18(2) | 19(2) | 0(1) | 6(2) | -3(2) |
| C(16) | 39(2) | 22(2) | 21(2) | -1(2) | 8(2) | -7(2) |
| C(17) | 24(2) | 20(2) | 14(2) | 1(1) | -1(1) | -1(1) |
| C(18) | 21(2) | 20(2) | 19(2) | -2(1) | -1(1) | 0(1) |
| C(21) | 19(2) | 23(2) | 16(2) | 0(1) | 3(1) | -2(1) |

FIG.15

(Table 4 — 2)

| | $U^{11}$ | $U^{22}$ | $U^{33}$ | $U^{23}$ | $U^{13}$ | $U^{12}$ |
|---|---|---|---|---|---|---|
| C(22) | 21(2) | 20(2) | 17(2) | 2(1) | 1(1) | 1(1) |
| C(23) | 25(2) | 24(2) | 15(2) | 2(1) | -1(1) | -2(2) |
| C(24) | 21(2) | 22(2) | 16(2) | 1(1) | 0(1) | 0(1) |
| C(25) | 20(2) | 13(2) | 16(2) | -3(1) | -1(1) | -1(1) |
| C(26) | 23(2) | 9(2) | 16(2) | -1(1) | 3(1) | 1(1) |
| C(27) | 21(2) | 31(2) | 15(2) | 1(2) | 0(1) | 2(2) |
| C(28) | 24(2) | 22(2) | 17(2) | 0(1) | -4(1) | -3(1) |
| C(29) | 20(2) | 33(2) | 24(2) | 4(2) | -2(2) | 3(2) |
| C(30) | 23(2) | 31(2) | 20(2) | 5(2) | -2(2) | 1(2) |
| C(31) | 21(2) | 15(2) | 15(2) | 1(1) | 0(1) | -1(1) |
| C(32) | 21(2) | 11(2) | 16(2) | 1(1) | 0(1) | 1(1) |
| C(33) | 23(2) | 30(2) | 19(2) | 5(2) | -6(2) | -5(2) |
| C(34) | 20(2) | 28(2) | 20(2) | 4(2) | 0(1) | -1(2) |
| C(35) | 23(2) | 18(2) | 18(2) | 2(1) | 2(1) | 1(1) |
| C(36) | 21(2) | 17(2) | 20(2) | 2(1) | -2(1) | 2(1) |
| C(37) | 23(2) | 14(2) | 12(2) | -1(1) | 1(1) | -2(1) |
| C(38) | 24(2) | 12(2) | 12(2) | 0(1) | 0(1) | 0(1) |
| N(1) | 23(2) | 20(2) | 18(2) | 1(1) | 2(1) | -1(1) |
| N(2) | 22(2) | 16(1) | 20(2) | -1(1) | -1(1) | -1(1) |
| N(3) | 23(2) | 20(2) | 14(1) | -1(1) | -2(1) | 1(1) |
| N(4) | 22(2) | 18(2) | 22(2) | -1(1) | 4(1) | -1(1) |
| N(5) | 25(2) | 17(2) | 17(2) | -1(1) | 2(1) | -1(1) |
| N(6) | 24(2) | 19(2) | 18(2) | -1(1) | -1(1) | -2(1) |
| N(21) | 20(2) | 16(1) | 16(2) | -1(1) | -2(1) | 1(1) |
| N(22) | 19(2) | 20(2) | 19(2) | 1(1) | 4(1) | -1(1) |
| N(23) | 23(2) | 15(1) | 16(2) | 1(1) | -4(1) | -4(1) |
| N(24) | 19(1) | 15(1) | 16(1) | -1(1) | 1(1) | 2(1) |
| N(25) | 19(1) | 15(1) | 16(1) | 0(1) | -1(1) | 1(1) |
| N(26) | 20(1) | 16(1) | 15(1) | 1(1) | 0(1) | -1(1) |
| C(101) | 36(2) | 12(2) | 32(2) | -4(2) | -2(2) | 0(2) |
| C(102) | 37(2) | 16(2) | 37(2) | -5(2) | -7(2) | 2(2) |
| C(103) | 33(2) | 20(2) | 36(2) | -4(2) | 3(2) | -4(2) |
| C(104) | 44(3) | 20(2) | 31(2) | 0(2) | 7(2) | -2(2) |

FIG.16

(Table 4 − 3)

| | $U^{11}$ | $U^{22}$ | $U^{33}$ | $U^{23}$ | $U^{13}$ | $U^{12}$ |
|---|---|---|---|---|---|---|
| C(105) | 42(2) | 22(2) | 28(2) | -1(2) | -1(2) | 2(2) |
| C(106) | 34(2) | 13(2) | 25(2) | 0(1) | 0(2) | 0(2) |
| C(107) | 38(2) | 11(2) | 26(2) | -3(1) | -1(2) | 0(2) |
| C(108) | 42(2) | 22(2) | 34(2) | 0(2) | -9(2) | -2(2) |
| C(109) | 46(3) | 24(2) | 45(3) | 2(2) | -13(2) | 3(2) |
| C(110) | 31(2) | 24(2) | 61(3) | -1(2) | -10(2) | -1(2) |
| C(111) | 37(2) | 19(2) | 42(3) | -3(2) | 1(2) | 0(2) |
| C(112) | 35(2) | 13(2) | 30(2) | -3(2) | 1(2) | 1(2) |
| C(113) | 43(2) | 10(2) | 27(2) | -2(1) | 1(2) | 2(2) |
| C(114) | 48(3) | 23(2) | 32(2) | -5(2) | 8(2) | 1(2) |
| C(115) | 64(3) | 23(2) | 23(2) | -3(2) | 10(2) | -4(2) |
| C(116) | 59(3) | 19(2) | 25(2) | -3(2) | -6(2) | -1(2) |
| C(117) | 45(3) | 17(2) | 31(2) | -3(2) | -7(2) | -1(2) |
| C(118) | 43(2) | 13(2) | 25(2) | -4(2) | -1(2) | 2(2) |
| O(101) | 41(2) | 41(2) | 35(2) | 1(1) | -8(1) | 2(2) |
| C(201) | 37(5) | 52(7) | 47(7) | 6(5) | 8(4) | -4(5) |
| C(202) | 73(7) | 75(9) | 43(6) | 15(6) | -5(5) | -6(6) |
| C(203) | 99(10) | 67(8) | 85(9) | 10(7) | -6(7) | -1(7) |
| C(204) | 62(9) | 84(12) | 84(13) | 25(9) | 6(7) | 4(8) |
| C(205) | 39(6) | 89(12) | 53(11) | 20(10) | -3(6) | -8(9) |
| C(206) | 16(4) | 108(14) | 47(9) | 0(7) | 3(5) | 3(7) |
| N(201) | 30(4) | 70(5) | 95(7) | 12(5) | 1(4) | 0(4) |
| O(201) | 97(10) | 105(11) | 67(9) | 42(7) | 18(6) | 38(7) |
| O(202) | 78(5) | 71(5) | 187(9) | 0(6) | -58(6) | -3(4) |
| C(211) | 26(9) | 43(11) | 39(12) | -22(9) | 11(8) | -23(8) |
| C(212) | 24(8) | 41(11) | 48(12) | -10(10) | -2(8) | -10(8) |
| C(213) | 32(12) | 59(18) | 55(15) | 2(14) | 3(11) | -11(12) |
| C(214) | 13(10) | 100(20) | 25(10) | -1(17) | -6(7) | -20(15) |
| C(215) | 10(8) | 89(19) | 36(13) | -13(12) | 5(8) | -5(12) |
| C(216) | 17(7) | 43(11) | 50(11) | -17(9) | 2(7) | -21(8) |
| N(211) | 27(6) | 38(8) | 38(7) | 1(6) | 9(5) | -8(5) |
| O(211) | 38(6) | 45(7) | 37(6) | -14(5) | 17(5) | -9(5) |
| O(212) | 62(14) | 35(8) | 66(17) | 9(10) | 35(13) | 8(8) |

FIG.17

(Table 4 — 4)

| | $U^{11}$ | $U^{22}$ | $U^{33}$ | $U^{23}$ | $U^{13}$ | $U^{12}$ |
|---|---|---|---|---|---|---|
| C(221) | 74(4) | 70(4) | 22(2) | 6(2) | 13(2) | 7(3) |
| C(222) | 74(4) | 81(5) | 27(3) | 11(3) | -6(3) | -28(4) |
| C(223) | 126(6) | 49(4) | 31(3) | 9(2) | -21(3) | -25(4) |
| C(224) | 107(6) | 88(5) | 24(3) | -1(3) | -20(3) | 42(5) |
| C(225) | 54(3) | 108(5) | 18(2) | 1(3) | -7(2) | -16(4) |
| C(226) | 89(5) | 51(3) | 21(2) | 2(2) | 9(3) | -19(3) |
| N(221) | 110(6) | 116(6) | 44(3) | 9(4) | 25(3) | 19(5) |
| O(221) | 102(5) | 275(10) | 84(4) | 50(5) | 56(4) | 64(6) |
| O(222) | 238(9) | 95(5) | 104(5) | -8(4) | 11(5) | 53(6) |
| C(231) | 36(3) | 49(3) | 41(3) | -5(2) | -7(2) | 6(2) |
| C(232) | 54(3) | 41(3) | 54(3) | 1(2) | -18(3) | 6(2) |
| C(233) | 61(4) | 53(3) | 48(3) | 4(3) | -22(3) | 2(3) |
| C(234) | 50(3) | 57(3) | 54(3) | -12(3) | -13(3) | 3(3) |
| C(235) | 63(4) | 53(3) | 63(4) | 1(3) | 5(3) | -16(3) |
| C(236) | 55(3) | 54(3) | 43(3) | 5(2) | 4(2) | -9(3) |
| N(231) | 51(3) | 50(3) | 46(3) | -3(2) | -10(2) | 12(2) |
| O(231) | 87(3) | 46(2) | 62(3) | -6(2) | -26(2) | 0(2) |
| O(232) | 64(3) | 78(3) | 35(2) | 0(2) | -8(2) | 20(2) |
| C(241) | 31(2) | 54(3) | 27(2) | 6(2) | -2(2) | 2(2) |
| C(242) | 42(3) | 57(3) | 35(3) | -6(2) | -6(2) | -5(2) |
| C(243) | 54(3) | 40(3) | 44(3) | 3(2) | -6(2) | -6(2) |
| C(244) | 53(3) | 48(3) | 32(3) | 8(2) | 3(2) | -8(2) |
| C(245) | 70(4) | 47(3) | 38(3) | 3(2) | 11(3) | 1(3) |
| C(246) | 63(3) | 44(3) | 36(3) | 5(2) | 6(2) | 5(2) |
| N(241) | 36(2) | 74(3) | 37(2) | 11(2) | -2(2) | 8(2) |
| O(241) | 63(3) | 113(4) | 27(2) | -3(2) | -10(2) | 14(2) |
| O(242) | 78(3) | 67(3) | 61(3) | 27(2) | 3(2) | 6(2) |
| C(301) | 54(4) | 108(6) | 78(5) | -42(4) | -7(3) | -2(4) |
| O(301) | 39(2) | 85(3) | 47(2) | -10(2) | -3(2) | -4(2) |

FIG.18

(Table 5)   Hydrogen coordinates ( x $10^4$) and isotropic displacement parameters ($Å^2$ x $10^3$) for pbca.

(Table 5 − 1)

|        | x    | y     | z     | U(eq) |
|--------|------|-------|-------|-------|
| H(1)   | 1935 | 11933 | -1341 | 27    |
| H(2)   | 1581 | 11095 | -959  | 29    |
| H(3)   | 2283 | 9461  | -1733 | 32    |
| H(4)   | 1933 | 8558  | -1360 | 27    |
| H(7)   | 645  | 5293  | -1271 | 27    |
| H(8)   | 939  | 6866  | -1201 | 27    |
| H(9)   | 692  | 4770  | -429  | 27    |
| H(10)  | 966  | 6346  | -336  | 29    |
| H(13)  | 303  | 9464  | 408   | 26    |
| H(14)  | 566  | 8584  | 8     | 26    |
| H(15)  | 1037 | 11795 | 151   | 28    |
| H(16)  | 1336 | 10971 | -256  | 33    |
| H(21)  | 774  | 10729 | 1302  | 23    |
| H(22)  | 1467 | 10501 | 1584  | 23    |
| H(23)  | 1590 | 11419 | 622   | 26    |
| H(24)  | 2306 | 11158 | 882   | 24    |
| H(27)  | 4289 | 11178 | 741   | 27    |
| H(28)  | 3509 | 10919 | 929   | 25    |
| H(29)  | 4893 | 10838 | 1512  | 31    |
| H(30)  | 4135 | 10552 | 1723  | 29    |
| H(33)  | 3324 | 9135  | 2729  | 29    |
| H(34)  | 3441 | 9720  | 2260  | 27    |
| H(35)  | 1892 | 9568  | 2676  | 23    |
| H(36)  | 1968 | 10147 | 2205  | 23    |
| H(103) | 3760 | 8361  | 1251  | 36    |
| H(104) | 3341 | 8713  | 822   | 38    |
| H(105) | 2484 | 8677  | 813   | 37    |

FIG.19

(Table 5 – 2)

|        | x        | y        | z        | U(eq)   |
|--------|----------|----------|----------|---------|
| H(108) | 1767     | 8553     | 790      | 39      |
| H(109) | 916      | 8627     | 776      | 46      |
| H(110) | 458      | 8410     | 1203     | 46      |
| H(111) | 852      | 8109     | 1636     | 39      |
| H(114) | 1191     | 7754     | 2002     | 41      |
| H(115) | 1576     | 7314     | 2434     | 44      |
| H(116) | 2436     | 7170     | 2448     | 41      |
| H(117) | 2904     | 7482     | 2043     | 37      |
| H(101) | 3815(18) | 8130(30) | 1701(10) | 42(13)  |
| H(202) | 2425     | 227      | 4718     | 77      |
| H(203) | 2146     | 1780     | 4584     | 101     |
| H(204) | 1760     | 2028     | 4149     | 92      |
| H(205) | 1715     | 825      | 3807     | 72      |
| H(206) | 1971     | -744     | 3927     | 68      |
| H(212) | 2319     | 1252     | 4554     | 45      |
| H(213) | 1900     | 1699     | 4090     | 59      |
| H(214) | 1640     | 386      | 3798     | 55      |
| H(215) | 1969     | -1085    | 3855     | 54      |
| H(216) | 2337     | -1497    | 4275     | 44      |
| H(222) | 2498     | 631      | 291      | 73      |
| H(223) | 3109     | -548     | 295      | 82      |
| H(224) | 3938     | -87      | 254      | 88      |
| H(225) | 4143     | 1570     | 213      | 72      |
| H(226) | 3520     | 2730     | 203      | 64      |
| H(232) | 5521     | -1153    | 2637     | 59      |
| H(233) | 5814     | -229     | 3025     | 65      |
| H(234) | 6046     | 1380     | 2958     | 64      |
| H(235) | 6030     | 2075     | 2497     | 71      |
| H(236) | 5750     | 1149     | 2096     | 61      |
| H(242) | 4427     | -855     | 2566     | 53      |
| H(243) | 4336     | -1511    | 3035     | 55      |
| H(244) | 4211     | -484     | 3430     | 53      |
| H(245) | 4180     | 1193     | 3366     | 62      |

FIG.20

(Table 5 − 3)

| | x | y | z | U(eq) |
|---|---|---|---|---|
| H(246) | 4282 | 1876 | 2901 | 57 |
| H(302) | 5060 | 8156 | 1534 | 96 |
| H(303) | 4613 | 7885 | 1322 | 96 |
| H(304) | 4816 | 7093 | 1548 | 96 |
| H(301) | 4660(30) | 8290(60) | 1960(20) | 150(30) |

FIG.21

(Table 6)   Crystal data and structure refinement for pbca.

| | |
|---|---|
| Identification code | pbca |
| Empirical formula | C78 H57 I6 N17 O7 Zn3 |
| Formula weight | 2301.92 |
| Temperature | 90(2) K |
| Wavelength | 0.71073 Å |
| Crystal system | Orthorhombic |
| Space group | Pbca |
| Unit cell dimensions | a = 27.265(5) Å    $\alpha$ = 90°. |
| | b = 13.710(3) Å    $\beta$ = 90°. |
| | c = 46.158(9) Å    $\gamma$ = 90°. |
| Volume | 17254(6) Å$^3$ |
| Z | 8 |
| Density (calculated) | 1.772 Mg/m$^3$ |
| Absorption coefficient | 3.035 mm$^{-1}$ |
| F(000) | 8864 |
| Crystal size | 0.60 x 0.35 x 0.30 mm$^3$ |
| Theta range for data collection | 1.72 to 28.83°. |
| Index ranges | -36<=h<=36, -18<=k<=18, -61<=l<=61 |
| Reflections collected | 194783 |
| Independent reflections | 21117 [R(int) = 0.0439] |
| Completeness to theta = 28.83° | 93.5 % |
| Absorption correction | None |
| Max. and min. transmission | 0.4629 and 0.2632 |
| Refinement method | Full-matrix least-squares on F$^2$ |
| Data / restraints / parameters | 21117 / 982 / 1505 |
| Goodness-of-fit on F$^2$ | 1.253 |
| Final R indices [I>2sigma(I)] | R1 = 0.0773, wR2 = 0.1499 |
| R indices (all data) | R1 = 0.0939, wR2 = 0.1572 |
| Largest diff. peak and hole | 2.168 and -1.733 e.Å$^{-3}$ |

FIG.22

(Table 7)  Atomic coordinates ( x 10⁴) and equivalent isotropic displacement parameters (Å²x 10³) for pbca.  U(eq) is defined as one third of the trace of the orthogonalized $U^{ij}$ tensor.

(Table 7 − 1)

|       | x        | y        | z        | U(eq)  |
|-------|----------|----------|----------|--------|
| Zn(1) | 2528(1)  | -1493(1) | 1901(1)  | 30(1)  |
| Zn(2) | 496(1)   | 1390(1)  | 4313(1)  | 23(1)  |
| Zn(3) | 5327(1)  | 1500(1)  | 4073(1)  | 27(1)  |
| I(1)  | 3040(1)  | -3043(1) | 1973(1)  | 40(1)  |
| I(2)  | 1616(1)  | -1615(1) | 1779(1)  | 50(1)  |
| I(3)  | -173(1)  | 433(1)   | 4054(1)  | 36(1)  |
| I(4)  | 456(1)   | 3215(1)  | 4423(1)  | 40(1)  |
| I(5)  | 5201(1)  | 2327(1)  | 4562(1)  | 43(1)  |
| I(6)  | 5793(1)  | 2290(1)  | 3659(1)  | 52(1)  |
| C(1)  | 4290(4)  | 4540(7)  | 1071(2)  | 43(2)  |
| C(2)  | 4115(4)  | 3602(7)  | 1037(2)  | 40(2)  |
| C(3)  | 4269(3)  | 4818(6)  | 585(2)   | 33(2)  |
| C(4)  | 4101(3)  | 3886(6)  | 531(2)   | 35(2)  |
| C(5)  | 4016(3)  | 3276(6)  | 760(2)   | 23(2)  |
| C(6)  | 3853(3)  | 2249(5)  | 714(2)   | 22(1)  |
| C(7)  | 4460(3)  | 255(6)   | -263(2)  | 25(2)  |
| C(8)  | 4310(3)  | 789(6)   | -26(2)   | 23(2)  |
| C(9)  | 4033(3)  | -1107(6) | -111(2)  | 29(2)  |
| C(10) | 3860(3)  | -604(6)  | 132(2)   | 29(2)  |
| C(11) | 3998(3)  | 352(5)   | 175(2)   | 22(1)  |
| C(12) | 3836(3)  | 895(6)   | 438(2)   | 24(2)  |
| C(13) | 3080(3)  | -1180(6) | 1360(2)  | 31(2)  |
| C(14) | 3287(3)  | -683(6)  | 1130(2)  | 29(2)  |
| C(15) | 2880(4)  | 257(7)   | 1582(2)  | 38(2)  |
| C(16) | 3083(3)  | 811(6)   | 1362(2)  | 34(2)  |
| C(17) | 3288(3)  | 322(6)   | 1128(2)  | 22(1)  |
| C(18) | 3514(3)  | 878(5)   | 886(2)   | 20(1)  |
| C(21) | 3045(3)  | -602(7)  | 2393(2)  | 36(2)  |

FIG.23

(Table 7 – 2)

|  | x | y | z | U(eq) |
|---|---|---|---|---|
| C(22) | 3119(3) | -268(6) | 2675(2) | 32(2) |
| C(23) | 2215(3) | -395(5) | 2425(2) | 25(2) |
| C(24) | 2252(3) | -46(5) | 2706(2) | 24(2) |
| C(25) | 2708(3) | 12(5) | 2835(1) | 21(1) |
| C(26) | 2765(3) | 307(5) | 3145(1) | 21(1) |
| C(27) | 1101(3) | 880(6) | 3794(2) | 24(2) |
| C(28) | 1506(3) | 721(6) | 3628(2) | 23(2) |
| C(29) | 1575(3) | 1250(6) | 4192(1) | 24(2) |
| C(30) | 2000(3) | 1101(6) | 4038(2) | 24(2) |
| C(31) | 1969(3) | 838(5) | 3748(1) | 17(1) |
| C(32) | 2418(3) | 679(5) | 3572(1) | 20(1) |
| C(33) | 4255(3) | 1070(6) | 4063(2) | 26(2) |
| C(34) | 3791(3) | 916(5) | 3955(2) | 22(1) |
| C(35) | 4598(3) | 993(7) | 3607(2) | 33(2) |
| C(36) | 4150(3) | 809(6) | 3485(2) | 31(2) |
| C(37) | 3732(3) | 798(5) | 3660(2) | 21(1) |
| C(38) | 3237(3) | 661(5) | 3530(2) | 22(1) |
| N(1) | 4374(2) | 5145(5) | 847(1) | 26(1) |
| N(2) | 4327(2) | -672(5) | -306(1) | 22(1) |
| N(3) | 2876(3) | -714(5) | 1585(1) | 29(1) |
| N(4) | 3957(2) | 1838(5) | 456(1) | 23(1) |
| N(5) | 3602(2) | 379(5) | 641(1) | 24(1) |
| N(6) | 3638(2) | 1801(5) | 936(1) | 23(1) |
| N(21) | 2610(2) | -698(5) | 2276(1) | 28(1) |
| N(22) | 1125(2) | 1133(5) | 4076(1) | 22(1) |
| N(23) | 4655(2) | 1122(5) | 3895(1) | 25(1) |
| N(24) | 2349(2) | 448(4) | 3292(1) | 19(1) |
| N(25) | 2852(2) | 795(4) | 3700(1) | 19(1) |
| N(26) | 3219(2) | 407(4) | 3247(1) | 21(1) |
| C(101) | 2366(7) | 3116(19) | 3505(4) | 47(4) |
| C(102) | 1866(7) | 3133(13) | 3477(5) | 55(4) |
| C(103) | 1559(7) | 3347(12) | 3717(5) | 51(4) |
| C(104) | 1806(7) | 3564(14) | 3984(5) | 54(4) |

FIG.24

(Table 7 − 3)

|   | x | y | z | U(eq) |
|---|---|---|---|---|
| C(105) | 2310(7) | 3575(19) | 4017(4) | 48(4) |
| C(106) | 2619(8) | 3330(50) | 3775(6) | 44(3) |
| C(107) | 3155(8) | 3330(40) | 3792(5) | 44(2) |
| C(108) | 3379(8) | 3490(20) | 4059(5) | 47(4) |
| C(109) | 3861(8) | 3542(16) | 4073(4) | 54(4) |
| C(110) | 4162(7) | 3418(12) | 3819(4) | 45(4) |
| C(111) | 3929(7) | 3227(16) | 3559(4) | 48(4) |
| C(112) | 3403(8) | 3180(20) | 3547(4) | 42(3) |
| C(113) | 3171(7) | 2951(18) | 3271(4) | 43(4) |
| C(114) | 3487(8) | 2745(14) | 3021(4) | 55(4) |
| C(115) | 3260(8) | 2467(12) | 2758(4) | 54(4) |
| C(116) | 2739(9) | 2406(16) | 2740(5) | 54(5) |
| C(117) | 2467(8) | 2589(12) | 2979(4) | 52(4) |
| C(118) | 2660(7) | 2876(16) | 3242(4) | 43(3) |
| N(101) | 1063(7) | 3360(12) | 3663(5) | 89(6) |
| C(121) | 3029(11) | 2920(30) | 3240(6) | 43(5) |
| C(122) | 3237(11) | 2660(20) | 2977(5) | 48(6) |
| C(123) | 2943(11) | 2440(30) | 2735(5) | 42(6) |
| C(124) | 2422(11) | 2446(19) | 2791(5) | 45(5) |
| C(125) | 2205(11) | 2680(20) | 3053(5) | 49(5) |
| C(126) | 2506(10) | 2930(30) | 3299(6) | 43(3) |
| C(127) | 2309(10) | 3180(30) | 3584(5) | 44(5) |
| C(128) | 1804(10) | 3230(20) | 3622(6) | 48(6) |
| C(129) | 1622(11) | 3430(20) | 3878(7) | 49(6) |
| C(130) | 1949(12) | 3620(20) | 4120(6) | 58(6) |
| C(131) | 2452(12) | 3580(30) | 4077(6) | 52(6) |
| C(132) | 2632(10) | 3390(80) | 3791(9) | 44(3) |
| C(133) | 3162(10) | 3320(80) | 3753(8) | 44(2) |
| C(134) | 3474(12) | 3560(40) | 4002(7) | 52(6) |
| C(135) | 3990(12) | 3550(30) | 3960(8) | 61(7) |
| C(136) | 4186(12) | 3370(30) | 3677(8) | 67(7) |
| C(137) | 3874(11) | 3210(30) | 3450(8) | 68(7) |
| C(138) | 3372(11) | 3150(40) | 3480(6) | 50(5) |

FIG.25

(Table 7 − 4)

|  | x | y | z | U(eq) |
|---|---|---|---|---|
| N(121) | 3152(11) | 2125(19) | 2482(4) | 71(8) |
| C(201) | 2959(5) | 1734(10) | 4768(2) | 67(3) |
| C(202) | 3431(5) | 2025(10) | 4786(2) | 69(4) |
| C(203) | 3794(5) | 1349(14) | 4783(2) | 84(5) |
| C(204) | 3683(7) | 392(13) | 4760(2) | 90(5) |
| C(205) | 3196(8) | 91(12) | 4743(3) | 98(5) |
| C(206) | 2829(6) | 801(11) | 4743(2) | 79(4) |
| N(201) | 2561(6) | 2528(12) | 4774(3) | 105(5) |
| O(201) | 2735(8) | 3346(12) | 4826(3) | 177(8) |
| O(202) | 2159(5) | 2235(15) | 4744(3) | 178(8) |
| C(211) | 2230(8) | -350(20) | 684(5) | 55(5) |
| C(212) | 2026(9) | -210(20) | 979(5) | 67(6) |
| C(213) | 1860(9) | 670(20) | 1033(6) | 68(6) |
| C(214) | 1913(10) | 1440(20) | 828(6) | 83(7) |
| C(215) | 2137(9) | 1280(20) | 558(5) | 84(7) |
| C(216) | 2297(9) | 380(20) | 487(5) | 67(6) |
| N(211) | 2395(5) | -1328(15) | 618(4) | 72(5) |
| O(211) | 2299(6) | -1972(14) | 791(5) | 126(7) |
| O(212) | 2651(7) | -1438(16) | 395(4) | 79(5) |
| C(221) | 2376(14) | -130(40) | 565(13) | 45(9) |
| C(222) | 2260(14) | -850(40) | 759(10) | 43(9) |
| C(223) | 2030(20) | -680(40) | 957(14) | 54(11) |
| C(224) | 1890(30) | 220(60) | 1034(18) | 68(6) |
| C(225) | 1982(16) | 990(40) | 877(11) | 47(9) |
| C(226) | 2245(13) | 790(40) | 604(9) | 37(8) |
| N(221) | 2682(8) | -398(19) | 315(5) | 31(6) |
| O(221) | 2771(16) | -1290(30) | 263(7) | 61(10) |
| O(222) | 2819(8) | 238(16) | 160(5) | 37(6) |
| C(231) | 9359(6) | 506(14) | 2700(3) | 53(4) |
| C(232) | 9339(10) | 1152(18) | 2929(5) | 86(7) |
| C(233) | 9281(10) | 780(19) | 3209(5) | 89(7) |
| C(234) | 9270(7) | -212(15) | 3245(4) | 68(5) |
| C(235) | 9315(7) | -828(14) | 3022(4) | 61(4) |

FIG.26

(Table 7 − 5)

|        | x         | y        | z        | U(eq)    |
|--------|-----------|----------|----------|----------|
| C(236) | 9364(6)   | -456(13) | 2742(4)  | 54(4)    |
| N(231) | 9408(6)   | 899(17)  | 2400(4)  | 81(5)    |
| O(231) | 9453(8)   | 1740(14) | 2359(4)  | 126(8)   |
| O(232) | 9438(6)   | 297(16)  | 2210(3)  | 102(6)   |
| C(241) | 9465(10)  | 4740(20) | 2724(7)  | 85(13)   |
| C(242) | 9421(14)  | 4390(30) | 2451(7)  | 73(13)   |
| C(243) | 9229(16)  | 4930(30) | 2235(8)  | 79(15)   |
| C(244) | 9090(20)  | 5850(30) | 2279(10) | 119(17)  |
| C(245) | 9140(20)  | 6250(30) | 2557(10) | 112(17)  |
| C(246) | 9301(18)  | 5650(30) | 2785(9)  | 91(15)   |
| N(241) | 9685(15)  | 4150(30) | 2976(7)  | 98(15)   |
| O(241) | 9843(16)  | 3340(20) | 2906(9)  | 123(19)  |
| O(242) | 9683(16)  | 4540(30) | 3205(7)  | 120(20)  |
| C(251) | 9877(12)  | -480(20) | 2039(7)  | 94(14)   |
| C(252) | 9720(12)  | 340(20)  | 2175(8)  | 78(14)   |
| C(253) | 10001(14) | 1160(20) | 2189(8)  | 76(13)   |
| C(254) | 10447(14) | 1150(30) | 2068(9)  | 69(12)   |
| C(255) | 10618(14) | 330(30)  | 1924(10) | 68(12)   |
| C(256) | 10323(14) | -520(30) | 1918(11) | 82(15)   |
| N(251) | 9547(13)  | -1380(20)| 2020(11) | 121(16)  |
| O(251) | 9157(16)  | -1280(40)| 2154(14) | 200(30)  |
| O(252) | 9717(16)  | -2060(20)| 1900(10) | 113(18)  |
| C(261) | 9450(11)  | 1950(20) | 3119(6)  | 100(13)  |
| C(262) | 9539(13)  | 1910(30) | 3408(6)  | 97(14)   |
| C(263) | 9840(15)  | 2550(30) | 3544(7)  | 107(16)  |
| C(264) | 10071(18) | 3230(30) | 3389(10) | 130(17)  |
| C(265) | 9980(20)  | 3320(40) | 3093(10) | 136(19)  |
| C(266) | 9663(18)  | 2640(30) | 2957(8)  | 123(17)  |
| N(261) | 9103(12)  | 1220(30) | 2969(7)  | 94(14)   |
| O(261) | 8938(13)  | 580(30)  | 3130(8)  | 115(17)  |
| O(262) | 9071(16)  | 1330(40) | 2716(7)  | 170(20)  |
| C(271) | 9203(9)   | 6140(30) | 2228(8)  | 233(19)  |
| C(272) | 9339(10)  | 5300(30) | 2099(7)  | 202(19)  |

FIG.27

(Table 7 — 6)

|  | x | y | z | U(eq) |
|---|---|---|---|---|
| C(273) | 9392(10) | 4450(30) | 2245(8) | 192(17) |
| C(274) | 9290(16) | 4460(30) | 2527(9) | 230(20) |
| C(275) | 9170(16) | 5320(40) | 2675(8) | 240(20) |
| C(276) | 9125(19) | 6190(30) | 2514(8) | 260(20) |
| N(271) | 9112(15) | 7090(30) | 2060(8) | 260(19) |
| O(271) | 9271(13) | 7010(30) | 1810(7) | 260(20) |
| O(272) | 9020(18) | 7780(30) | 2211(10) | 310(30) |
| C(301) | 9360(30) | 5380(50) | 2073(16) | 22(17) |
| O(301) | 9400(40) | 4530(60) | 1890(20) | 110(30) |
| C(311) | 9930(20) | 4430(40) | 1869(16) | 70(20) |
| O(311) | 9660(20) | 5310(40) | 1850(11) | 83(18) |

FIG.28

(Table 8)   Anisotropic displacement parameters ($Å^2 \times 10^3$) for pbca.   The anisotropic displacement factor exponent takes the form: $-2\pi^2[ h^2 a^{*2} U^{11} + ... + 2 h k a^* b^* U^{12} ]$ (Table 8 − 1)

|       | $U^{11}$ | $U^{22}$ | $U^{33}$ | $U^{23}$ | $U^{13}$ | $U^{12}$ |
|-------|------|------|------|-------|-------|--------|
| Zn(1) | 39(1) | 36(1) | 14(1) | -8(1) | 6(1) | -10(1) |
| Zn(2) | 23(1) | 32(1) | 15(1) | 0(1) | 1(1) | 3(1) |
| Zn(3) | 22(1) | 23(1) | 37(1) | -1(1) | -4(1) | 2(1) |
| I(1) | 58(1) | 32(1) | 31(1) | 0(1) | 7(1) | -6(1) |
| I(2) | 41(1) | 75(1) | 34(1) | -26(1) | -1(1) | -11(1) |
| I(3) | 21(1) | 59(1) | 29(1) | -9(1) | -1(1) | 1(1) |
| I(4) | 45(1) | 30(1) | 45(1) | 1(1) | -3(1) | 11(1) |
| I(5) | 40(1) | 40(1) | 50(1) | -24(1) | -16(1) | 10(1) |
| I(6) | 42(1) | 49(1) | 65(1) | 18(1) | 7(1) | -13(1) |
| C(1) | 73(7) | 32(5) | 24(4) | -7(3) | 10(4) | -20(5) |
| C(2) | 67(6) | 31(5) | 23(4) | -3(3) | 12(4) | -17(4) |
| C(3) | 53(5) | 22(4) | 23(4) | 5(3) | -8(4) | 1(4) |
| C(4) | 57(6) | 28(4) | 21(4) | -2(3) | -15(4) | -7(4) |
| C(5) | 22(3) | 26(4) | 23(3) | 3(3) | -5(3) | -1(3) |
| C(6) | 21(3) | 25(4) | 20(3) | -3(3) | -2(3) | 1(3) |
| C(7) | 29(4) | 25(4) | 20(3) | 2(3) | -2(3) | -5(3) |
| C(8) | 24(4) | 25(4) | 20(3) | 1(3) | 2(3) | -5(3) |
| C(9) | 41(5) | 23(4) | 22(4) | -2(3) | 4(3) | -10(3) |
| C(10) | 39(4) | 29(4) | 19(3) | 2(3) | 5(3) | -4(3) |
| C(11) | 28(4) | 21(4) | 17(3) | 4(3) | -2(3) | -3(3) |
| C(12) | 26(4) | 27(4) | 17(3) | 2(3) | -3(3) | 5(3) |
| C(13) | 34(4) | 33(4) | 25(4) | -7(3) | 7(3) | -2(3) |
| C(14) | 36(4) | 27(4) | 23(4) | -9(3) | 13(3) | 0(3) |
| C(15) | 55(6) | 36(5) | 24(4) | -9(3) | 20(4) | 3(4) |
| C(16) | 50(5) | 24(4) | 28(4) | -4(3) | 12(4) | -2(4) |
| C(17) | 21(3) | 28(4) | 18(3) | -6(3) | 3(3) | -3(3) |
| C(18) | 18(3) | 23(4) | 20(3) | -2(3) | -1(3) | -1(3) |
| C(21) | 30(4) | 53(6) | 25(4) | -11(4) | 11(3) | -12(4) |

FIG.29

(Table 8 – 2)

| | $U^{11}$ | $U^{22}$ | $U^{33}$ | $U^{23}$ | $U^{13}$ | $U^{12}$ |
|---|---|---|---|---|---|---|
| C(22) | 30(4) | 44(5) | 24(4) | -9(3) | 0(3) | -12(4) |
| C(23) | 37(4) | 21(4) | 16(3) | -2(3) | -5(3) | -1(3) |
| C(24) | 30(4) | 24(4) | 19(3) | -3(3) | 1(3) | 3(3) |
| C(25) | 30(4) | 17(3) | 16(3) | -1(3) | 3(3) | -7(3) |
| C(26) | 33(4) | 22(4) | 9(3) | 3(2) | -1(3) | -5(3) |
| C(27) | 22(3) | 32(4) | 17(3) | 2(3) | -3(3) | -3(3) |
| C(28) | 25(4) | 29(4) | 15(3) | -4(3) | 1(3) | -2(3) |
| C(29) | 32(4) | 30(4) | 10(3) | -4(3) | 3(3) | -5(3) |
| C(30) | 23(3) | 30(4) | 18(3) | -4(3) | -4(3) | -3(3) |
| C(31) | 24(3) | 14(3) | 14(3) | -1(2) | 3(3) | -3(3) |
| C(32) | 28(4) | 18(3) | 14(3) | 5(2) | -2(3) | -1(3) |
| C(33) | 30(4) | 33(4) | 14(3) | 0(3) | -1(3) | -4(3) |
| C(34) | 24(4) | 23(4) | 19(3) | 2(3) | 3(3) | -1(3) |
| C(35) | 26(4) | 47(5) | 24(4) | 1(4) | 4(3) | -1(4) |
| C(36) | 29(4) | 40(5) | 23(4) | -6(3) | 3(3) | 2(3) |
| C(37) | 25(4) | 19(3) | 17(3) | 0(3) | -2(3) | 0(3) |
| C(38) | 27(4) | 19(3) | 20(3) | 4(3) | 0(3) | 0(3) |
| N(1) | 23(3) | 22(3) | 31(3) | 3(3) | -3(3) | -5(3) |
| N(2) | 24(3) | 26(3) | 15(3) | 0(2) | -2(2) | 3(3) |
| N(3) | 39(4) | 27(3) | 20(3) | -5(3) | 7(3) | -2(3) |
| N(4) | 27(3) | 24(3) | 20(3) | 2(2) | 0(2) | 2(3) |
| N(5) | 27(3) | 26(3) | 19(3) | -5(2) | -1(2) | -4(3) |
| N(6) | 21(3) | 27(3) | 21(3) | -1(2) | 3(2) | 2(2) |
| N(21) | 32(4) | 34(4) | 16(3) | -8(3) | 8(2) | -9(3) |
| N(22) | 23(3) | 26(3) | 17(3) | 0(2) | 3(2) | 4(2) |
| N(23) | 20(3) | 29(3) | 27(3) | 0(3) | -2(2) | 0(3) |
| N(24) | 27(3) | 16(3) | 13(3) | -1(2) | -1(2) | -3(2) |
| N(25) | 24(3) | 18(3) | 15(3) | 2(2) | 1(2) | 0(2) |
| N(26) | 23(3) | 21(3) | 19(3) | -1(2) | -1(2) | -4(2) |
| C(101) | 63(7) | 21(6) | 56(8) | 9(7) | -8(7) | -9(6) |
| C(102) | 70(9) | 27(7) | 69(9) | 20(8) | -7(8) | -2(7) |
| C(103) | 68(9) | 22(6) | 62(10) | 16(7) | -7(8) | -2(7) |
| C(104) | 71(9) | 34(8) | 59(10) | 7(8) | -2(8) | 6(8) |

FIG.30

(Table 8 – 3)

| | $U^{11}$ | $U^{22}$ | $U^{33}$ | $U^{23}$ | $U^{13}$ | $U^{12}$ |
|---|---|---|---|---|---|---|
| C(105) | 70(9) | 24(7) | 49(8) | 13(7) | 1(7) | 6(8) |
| C(106) | 77(5) | 18(6) | 38(4) | 9(4) | 1(4) | -1(4) |
| C(107) | 79(5) | 14(3) | 38(6) | 7(6) | -9(4) | -3(4) |
| C(108) | 67(9) | 26(7) | 48(8) | 10(7) | -14(7) | -1(8) |
| C(109) | 78(10) | 35(7) | 49(8) | 5(7) | -13(8) | -7(8) |
| C(110) | 65(9) | 25(7) | 44(8) | -5(7) | -8(7) | -3(6) |
| C(111) | 73(9) | 32(7) | 41(8) | 2(7) | -16(7) | -6(7) |
| C(112) | 72(8) | 20(6) | 34(7) | -1(6) | -11(6) | -12(6) |
| C(113) | 80(8) | 18(6) | 30(6) | 2(5) | -16(6) | -11(7) |
| C(114) | 72(9) | 36(7) | 57(8) | 21(7) | -10(8) | -14(8) |
| C(115) | 98(11) | 26(7) | 40(8) | 22(6) | 1(8) | -6(8) |
| C(116) | 99(12) | 22(7) | 43(9) | 17(7) | -16(9) | -6(9) |
| C(117) | 85(10) | 27(7) | 45(8) | 10(6) | -31(8) | -6(8) |
| C(118) | 78(7) | 14(4) | 39(5) | 8(4) | -11(6) | -6(6) |
| N(101) | 108(14) | 47(9) | 111(14) | 28(10) | -2(12) | -7(10) |
| C(121) | 79(11) | 19(8) | 31(9) | 4(8) | 4(9) | 5(10) |
| C(122) | 89(13) | 27(10) | 28(10) | 0(8) | 11(11) | 12(11) |
| C(123) | 90(14) | 25(10) | 11(9) | -2(8) | 13(10) | 9(12) |
| C(124) | 95(14) | 30(9) | 10(8) | -4(7) | 8(10) | 4(11) |
| C(125) | 94(13) | 28(9) | 25(9) | -2(8) | -4(10) | -1(11) |
| C(126) | 78(7) | 14(4) | 39(5) | 8(4) | -11(6) | -6(6) |
| C(127) | 77(10) | 15(8) | 38(9) | 13(8) | 3(8) | -3(8) |
| C(128) | 81(12) | 18(9) | 44(11) | 14(10) | 11(11) | 6(10) |
| C(129) | 82(14) | 24(10) | 42(12) | 17(10) | 15(11) | 4(10) |
| C(130) | 96(14) | 30(10) | 48(12) | 13(10) | 16(12) | 6(11) |
| C(131) | 93(13) | 24(10) | 39(10) | 12(9) | 6(11) | 0(11) |
| C(132) | 77(5) | 18(6) | 38(4) | 9(4) | 1(4) | -1(4) |
| C(133) | 79(5) | 14(3) | 38(6) | 7(6) | -9(4) | -3(4) |
| C(134) | 83(13) | 27(10) | 48(12) | 3(11) | -14(11) | -14(11) |
| C(135) | 92(14) | 33(11) | 58(14) | -6(13) | -8(13) | -18(12) |
| C(136) | 99(14) | 33(11) | 70(15) | -1(13) | -11(13) | -9(11) |
| C(137) | 95(14) | 38(11) | 73(14) | 2(13) | 3(13) | 4(11) |
| C(138) | 80(10) | 21(9) | 49(11) | 5(10) | 6(10) | 6(9) |

FIG.31

(Table 8 − 4)

| | $U^{11}$ | $U^{22}$ | $U^{33}$ | $U^{23}$ | $U^{13}$ | $U^{12}$ |
|---|---|---|---|---|---|---|
| N(121) | 130(20) | 62(15) | 24(11) | 4(11) | 8(13) | -3(15) |
| C(201) | 84(9) | 87(9) | 29(5) | -14(5) | -22(5) | 6(7) |
| C(202) | 105(10) | 79(9) | 22(5) | -2(5) | -6(6) | -18(8) |
| C(203) | 80(9) | 153(14) | 18(5) | -8(7) | 9(5) | -27(10) |
| C(204) | 131(13) | 110(12) | 29(6) | -2(7) | 30(7) | 51(11) |
| C(205) | 175(16) | 76(10) | 43(7) | 4(7) | 31(9) | -26(11) |
| C(206) | 110(11) | 96(10) | 32(6) | -9(6) | 16(6) | -31(9) |
| N(201) | 139(13) | 109(11) | 66(8) | -13(8) | -38(9) | 0(11) |
| O(201) | 290(20) | 136(14) | 105(11) | 6(11) | -38(13) | 44(15) |
| O(202) | 132(12) | 310(20) | 91(9) | -62(12) | -74(9) | 57(14) |
| C(211) | 36(9) | 85(14) | 45(10) | -9(10) | -11(8) | 0(11) |
| C(212) | 39(9) | 112(18) | 51(10) | -30(13) | -6(7) | 25(13) |
| C(213) | 41(7) | 109(18) | 54(8) | -25(14) | 0(6) | 21(13) |
| C(214) | 76(14) | 93(16) | 79(15) | -29(14) | -14(12) | 6(13) |
| C(215) | 96(16) | 84(15) | 72(13) | -17(12) | -12(12) | 13(13) |
| C(216) | 72(13) | 78(15) | 52(11) | -11(11) | -7(10) | -8(12) |
| N(211) | 34(7) | 93(12) | 88(12) | 3(11) | 5(7) | -3(8) |
| O(211) | 91(12) | 112(14) | 175(19) | 6(13) | 65(12) | -16(10) |
| O(212) | 88(12) | 100(13) | 50(9) | -32(10) | -15(9) | 19(9) |
| C(221) | 15(14) | 60(20) | 60(20) | -18(18) | -1(14) | 5(15) |
| C(222) | 14(14) | 70(20) | 50(20) | -21(19) | -16(14) | 5(17) |
| C(223) | 25(16) | 70(20) | 70(20) | -30(20) | -3(16) | 10(20) |
| C(224) | 41(7) | 109(18) | 54(8) | -25(14) | 0(6) | 21(13) |
| C(225) | 26(15) | 70(20) | 43(18) | 13(19) | 11(14) | 10(17) |
| C(226) | 23(14) | 50(20) | 38(17) | -7(17) | 3(13) | 5(14) |
| N(221) | 23(11) | 37(13) | 32(12) | 4(10) | -17(9) | -5(10) |
| O(221) | 70(20) | 70(20) | 36(17) | -21(18) | -23(17) | 39(18) |
| O(222) | 37(12) | 41(13) | 32(11) | 4(9) | -8(9) | 5(10) |
| C(231) | 48(8) | 81(11) | 31(7) | 10(7) | -4(6) | 15(8) |
| C(232) | 119(18) | 79(13) | 61(12) | 31(10) | 6(13) | 36(13) |
| C(233) | 111(16) | 96(15) | 59(11) | 29(11) | 4(12) | 22(14) |
| C(234) | 61(10) | 79(12) | 62(10) | 36(9) | 14(8) | 9(9) |
| C(235) | 67(11) | 58(10) | 59(10) | 14(8) | -7(8) | -5(8) |

FIG.32

(Table 8 − 5)

| | $U^{11}$ | $U^{22}$ | $U^{33}$ | $U^{23}$ | $U^{13}$ | $U^{12}$ |
|---|---|---|---|---|---|---|
| C(236) | 45(8) | 67(10) | 49(8) | -10(8) | -10(7) | 9(8) |
| N(231) | 69(10) | 126(15) | 46(9) | 29(10) | -12(8) | -5(10) |
| O(231) | 180(20) | 104(14) | 95(13) | 60(11) | 10(12) | -22(13) |
| O(232) | 82(11) | 191(19) | 32(7) | 6(9) | -5(7) | 8(12) |
| C(241) | 70(20) | 90(30) | 90(20) | -50(20) | -10(20) | -40(20) |
| C(242) | 50(20) | 80(30) | 90(30) | -20(20) | 20(20) | -40(20) |
| C(243) | 70(30) | 90(30) | 80(30) | -50(20) | 0(20) | -10(20) |
| C(244) | 100(30) | 130(30) | 130(30) | -50(30) | -20(30) | 30(30) |
| C(245) | 70(30) | 110(30) | 150(40) | -70(30) | 20(30) | 50(20) |
| C(246) | 60(30) | 100(30) | 100(30) | -70(30) | 20(20) | 20(20) |
| N(241) | 100(30) | 110(30) | 90(30) | -60(20) | 20(20) | -50(20) |
| O(241) | 140(40) | 110(40) | 120(40) | -40(30) | 30(30) | -70(30) |
| O(242) | 100(30) | 180(50) | 90(30) | -100(30) | 40(20) | -60(30) |
| C(251) | 60(20) | 90(30) | 140(30) | 50(20) | 0(20) | 20(20) |
| C(252) | 30(20) | 100(30) | 100(30) | 50(20) | 10(20) | 20(20) |
| C(253) | 50(20) | 100(30) | 80(30) | 30(20) | 0(20) | 10(20) |
| C(254) | 70(20) | 70(20) | 60(20) | 20(20) | -10(20) | -10(20) |
| C(255) | 80(30) | 50(20) | 70(30) | 30(20) | 20(20) | 10(20) |
| C(256) | 80(30) | 60(30) | 100(30) | 30(30) | 0(30) | 20(20) |
| N(251) | 60(30) | 110(30) | 190(40) | 30(30) | 40(30) | 20(20) |
| O(251) | 120(50) | 170(60) | 310(70) | 10(60) | 70(50) | 50(40) |
| O(252) | 110(30) | 70(20) | 160(40) | -90(30) | 60(30) | -20(20) |
| C(261) | 130(30) | 120(30) | 50(20) | 20(20) | 20(20) | 60(20) |
| C(262) | 140(30) | 100(30) | 50(20) | 10(20) | 30(20) | 60(30) |
| C(263) | 170(40) | 90(30) | 60(20) | 0(20) | 30(30) | 40(30) |
| C(264) | 200(40) | 100(30) | 90(30) | 0(30) | 50(30) | 30(30) |
| C(265) | 190(40) | 120(40) | 100(30) | 30(30) | 20(30) | 40(30) |
| C(266) | 170(40) | 120(30) | 80(30) | 30(30) | 30(30) | 50(30) |
| N(261) | 60(20) | 160(30) | 60(20) | 0(20) | 9(19) | 70(20) |
| O(261) | 60(20) | 210(50) | 80(30) | -40(30) | 10(20) | -30(30) |
| O(262) | 130(40) | 300(60) | 80(30) | -20(40) | -30(30) | 130(40) |
| C(271) | 170(30) | 370(40) | 150(30) | 40(30) | 0(30) | -60(30) |
| C(272) | 130(30) | 390(50) | 80(20) | 0(30) | -20(20) | -150(30) |

FIG.33

(Table 8 — 6)

|        | $U^{11}$ | $U^{22}$ | $U^{33}$ | $U^{23}$ | $U^{13}$ | $U^{12}$ |
|--------|----------|----------|----------|----------|----------|----------|
| C(273) | 120(20)  | 370(40)  | 90(20)   | 50(30)   | -51(18)  | -180(30) |
| C(274) | 130(30)  | 360(50)  | 210(30)  | 100(30)  | 0(30)    | -150(30) |
| C(275) | 110(20)  | 360(50)  | 230(30)  | 120(30)  | 50(30)   | -90(30)  |
| C(276) | 160(30)  | 380(50)  | 230(40)  | 60(40)   | 50(30)   | -50(30)  |
| N(271) | 220(30)  | 400(50)  | 160(30)  | -30(30)  | -80(30)  | 10(40)   |
| O(271) | 300(40)  | 330(40)  | 170(30)  | -80(30)  | -160(30) | 80(40)   |
| O(272) | 310(50)  | 290(50)  | 340(50)  | -70(50)  | -20(40)  | 60(50)   |

FIG.34

(Table 9)  Hydrogen coordinates ($\times 10^4$) and isotropic displacement parameters ($\text{Å}^2 \times 10^3$) for pbca.

(Table 9 — 1)

|        | x    | y     | z    | U(eq) |
|--------|------|-------|------|-------|
| H(1A)  | 4353 | 4769  | 1262 | 51    |
| H(2A)  | 4065 | 3190  | 1199 | 49    |
| H(3A)  | 4311 | 5247  | 425  | 39    |
| H(4A)  | 4045 | 3672  | 338  | 42    |
| H(7A)  | 4667 | 560   | -402 | 30    |
| H(8A)  | 4418 | 1442  | 0    | 28    |
| H(9A)  | 3942 | -1770 | -138 | 34    |
| H(10A) | 3649 | -919  | 267  | 35    |
| H(13A) | 3082 | -1872 | 1359 | 37    |
| H(14A) | 3429 | -1034 | 974  | 34    |
| H(15A) | 2734 | 590   | 1741 | 46    |
| H(16A) | 3083 | 1504  | 1371 | 41    |
| H(21A) | 3325 | -769  | 2280 | 43    |
| H(22A) | 3439 | -231  | 2756 | 39    |
| H(23A) | 1901 | -419  | 2336 | 30    |
| H(24A) | 1967 | 151   | 2809 | 29    |
| H(27A) | 787  | 810   | 3707 | 28    |
| H(28A) | 1472 | 530   | 3431 | 28    |
| H(29A) | 1599 | 1445  | 4389 | 29    |
| H(30A) | 2311 | 1177  | 4129 | 28    |
| H(33A) | 4293 | 1142  | 4267 | 31    |
| H(34A) | 3516 | 892   | 4081 | 27    |
| H(35A) | 4878 | 1031  | 3485 | 39    |
| H(36A) | 4123 | 690   | 3282 | 37    |
| H(10B) | 1722 | 3000  | 3294 | 66    |
| H(10C) | 1611 | 3709  | 4149 | 65    |
| H(10D) | 2452 | 3745  | 4198 | 57    |

FIG.35

(Table 9 − 2)

|        | x    | y    | z    | U(eq) |
|--------|------|------|------|-------|
| H(10E) | 3187 | 3562 | 4229 | 57    |
| H(10F) | 4013 | 3662 | 4255 | 65    |
| H(11A) | 4509 | 3467 | 3829 | 54    |
| H(11B) | 4117 | 3125 | 3388 | 58    |
| H(11C) | 3833 | 2796 | 3036 | 66    |
| H(11D) | 3455 | 2321 | 2594 | 65    |
| H(11E) | 2585 | 2240 | 2562 | 65    |
| H(11F) | 2121 | 2515 | 2965 | 63    |
| H(10G) | 952  | 3240 | 3488 | 107   |
| H(10H) | 856  | 3489 | 3804 | 107   |
| H(12A) | 3583 | 2641 | 2960 | 58    |
| H(12B) | 2210 | 2280 | 2635 | 54    |
| H(12C) | 1858 | 2670 | 3071 | 59    |
| H(12D) | 1591 | 3125 | 3462 | 57    |
| H(12E) | 1276 | 3446 | 3906 | 59    |
| H(13B) | 1819 | 3780 | 4305 | 70    |
| H(13C) | 2673 | 3664 | 4235 | 63    |
| H(13D) | 3336 | 3708 | 4185 | 63    |
| H(13E) | 4204 | 3658 | 4119 | 73    |
| H(13F) | 4531 | 3366 | 3647 | 81    |
| H(13G) | 4010 | 3138 | 3262 | 82    |
| H(12F) | 3473 | 2067 | 2469 | 85    |
| H(12G) | 2966 | 1984 | 2332 | 85    |
| H(20A) | 3509 | 2698 | 4802 | 82    |
| H(20B) | 4127 | 1548 | 4797 | 100   |
| H(20C) | 3938 | -79  | 4755 | 108   |
| H(20D) | 3116 | -582 | 4732 | 117   |
| H(20E) | 2494 | 623  | 4725 | 95    |
| H(21B) | 2016 | -715 | 1119 | 81    |
| H(21C) | 1700 | 797  | 1212 | 82    |
| H(21D) | 1795 | 2073 | 875  | 99    |
| H(21E) | 2176 | 1804 | 425  | 101   |
| H(21F) | 2450 | 252  | 306  | 81    |

FIG.36

(Table 9 — 3)

|  | x | y | z | U(eq) |
|---|---|---|---|---|
| H(22B) | 2374 | -1493 | 728 | 52 |
| H(22C) | 1930 | -1207 | 1076 | 65 |
| H(22D) | 1711 | 300 | 1210 | 82 |
| H(22E) | 1887 | 1625 | 934 | 57 |
| H(22F) | 2315 | 1287 | 467 | 44 |
| H(23B) | 9364 | 1835 | 2897 | 104 |
| H(23C) | 9249 | 1205 | 3370 | 106 |
| H(23D) | 9229 | -470 | 3435 | 81 |
| H(23E) | 9313 | -1513 | 3054 | 74 |
| H(23F) | 9401 | -886 | 2582 | 65 |
| H(24B) | 9529 | 3743 | 2411 | 87 |
| H(24C) | 9188 | 4646 | 2048 | 95 |
| H(24D) | 8970 | 6238 | 2124 | 143 |
| H(24E) | 9061 | 6913 | 2591 | 134 |
| H(24F) | 9296 | 5879 | 2979 | 109 |
| H(25A) | 9405 | 345 | 2262 | 94 |
| H(25B) | 9882 | 1726 | 2284 | 92 |
| H(25C) | 10648 | 1717 | 2081 | 83 |
| H(25D) | 10929 | 334 | 1831 | 82 |
| H(25E) | 10438 | -1100 | 1830 | 99 |
| H(26A) | 9384 | 1412 | 3519 | 117 |
| H(26B) | 9886 | 2513 | 3747 | 129 |
| H(26C) | 10299 | 3655 | 3479 | 156 |
| H(26D) | 10121 | 3830 | 2984 | 164 |
| H(26E) | 9605 | 2672 | 2754 | 147 |
| H(27B) | 9400 | 5308 | 1896 | 243 |
| H(27C) | 9497 | 3872 | 2150 | 230 |
| H(27D) | 9300 | 3863 | 2631 | 279 |
| H(27E) | 9119 | 5312 | 2878 | 283 |
| H(27F) | 9042 | 6787 | 2605 | 307 |

FIG.37
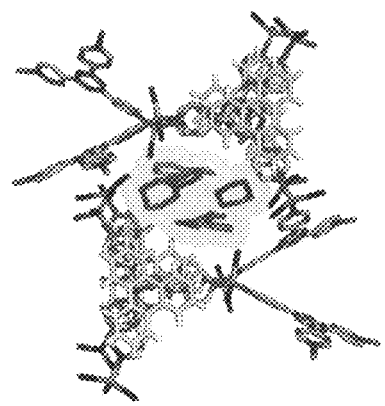
(37A)
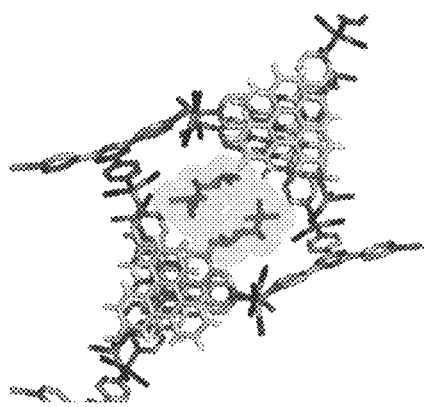
(37B)

POLYMER COMPLEX

CROSS-REFERENCE TO RELATED APPLICATIONS

This application is a national phase application of International Application No. PCT/JP2007/054600, filed Mar. 2, 2007, and claims the priority of Japanese Application No. 2006-063416, filed Mar. 8, 2006, the contents of both of which are incorporated herein by reference.

TECHNICAL FIELD

The present invention relates to a polymer complex.

BACKGROUND ART

By allowing a mixture containing many kinds of organic compounds to be passed through, or contacted with, a material having a pore structure which takes a guest compound in, a specific organic compound can be selectively taken out. As such material, an organic metal complex having organic ligands complexed with a transition metal, or zeolite or the like, is known and used in many applications as a selective reversible adsorbent, a catalyst carrier, etc.

DISCLOSURE OF THE INVENTION

Problem to be Solved by the Invention

However, the environments of channels (internal environments of channels) contained in a structure of zeolite or the like are uniform, and relatively large channels different in environment hardly coexist in a single zeolite material. Accordingly, two or more kinds of channels capable of selective incorporation of compounds having a relatively large molecular size, such as organic compounds, conventionally hardly coexist in a single material having an action of incorporating guest compounds.

On the other hand, techniques of producing fuel alcohols such as ethanol by utilizing biomass resources attract attention in recent years, but at present, the process for converting biomass resources into alcohol etc. is a complicated process with low efficiency. Particularly, the concentration of purified alcohol requires tremendous energy. Accordingly, energy-saving separation technology utilizing a molecular sieve effect attracts attention as technology contributing to improvement in energy efficiency in processes such as separation and purification of alcohol etc. As a method of concentrating ethanol by utilizing the molecular sieve effect of zeolite or the like for example, there is a method wherein hydrophobated zeolite is used to selectively capture ethanol from an ethanol mixture, and the captured ethanol is brought out by differential pressure (vacuuming) to give a highly concentrated ethanol solution (alcohol concentration: about 90%), and then hydrophilized zeolite is used to selectively capture water from the highly concentrated ethanol solution, thereby further increasing the concentration of ethanol.

In view of the circumstances described above, some of the present inventors have developed a polymer complex comprising an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between the aromatic compound ligands in a three-dimensional coordination network formed by coordinating the aromatic compound ligands to the central metal ion, and the three-dimensional lattice-like structure is provided with two or more kinds of channel groups each composed of channels identical with one another and having inherent affinity for guest components, and they have already filed a patent application therefor (Japanese Patent Application No. 2004-382152).

The present invention has further been developed through the history of development described above, and the object of the present invention is to provide a polymer complex having two or more kinds of channel groups through which specific compounds ranging from gaseous small molecules to large molecules such as proteins and other biomolecules can be selectively incorporated and/or released and/or transported.

Means for Solving the Problem

The polymer complex of the present invention comprises an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between the aromatic compound ligands in a three-dimensional coordination network formed by coordinating the aromatic compound ligands to the central metal ion, the three-dimensional lattice-like structure is provided with two or more kinds of channel groups each composed of channels identical with one another and having inherent affinity for guest components, the uncoordinating aromatic compound has a specific substituent A at a specific position on the aromatic ring thereof, and the uncoordinating aromatic compound is arranged regularly such that the substituent A is directed to the inside of a specific channel group B out of the two or more kinds of channel groups.

A channel group formed in the polymer complex for which some of the present inventors have filed a patent application (Japanese Patent Application No. 2004-382152) is composed of a plurality of mutually identical channels having inherent affinity, wherein channels constituting the channel group upon contacting with a mixture containing two or more kinds of components will selectively incorporate a component for which the channels have affinity out of a plurality of components contained in the mixture with which they have contacted. Because two or more kinds of channel groups exist in the polymer complex, two or more guest components can be incorporated by the polymer complex as a whole. Further, two or more guest components that were incorporated into the polymer complex exist in such a state that the guest components are separated from one another by the respective channel groups in the polymer complex. The guest components that were incorporated into channels can also be selectively released or transported.

The polymer complex of the present invention is a improvement to the polymer complex for which the patent application (Japanese Patent Application No. 2004-382152) has already been filed, wherein said improvement comprises introducing a specific substituent A into an aromatic ring of the uncoordinating aromatic compound, thereby modifying a specific channel group B among the two or more kinds of channel groups having inherent affinity for specific guest components, thus regulating characteristics of the channel environment of the channel group B.

The channel environment (size, shape, atmosphere etc.) of the channel group B significantly vary depending on the type, number and introducing position of substituents A introduced into the uncoordinating aromatic compound. That is, the channel environment of the channel group B can be regulated at will by changing the type, number and introducing position of substituents A to be introduced into the uncoordinating aromatic compound. Accordingly, the introduction of substituent A into the aromatic ring of the uncoordinating aromatic compound brings an improvement in the affinity inherent in the channel group B for the corresponding guest component, as well as impartment of new affinity on the channel group B, thus changing the affinity of the channel group B for the guest component, to achieve an improvement in the selectivity of the polymer complex for the guest component.

By introducing the substituent A into the uncoordinating aromatic compound, the polymer complex of the present invention can easily regulate the environmental characteristics of channels contained in a channel group formed in the polymer complex as described above, so that compounds having various characteristics, ranging from gaseous small molecules to large molecules such as proteins and other biomolecules, can be incorporated into the channels. That is, each of the channel groups can incorporate a specific compound selectively from a mixture containing two or more kinds of small-molecule to large-molecule compounds.

Further, the regularity of a three-dimensional lattice-like structure of the polymer complex, that is, the structural regularity of the channel group, can be increased by introducing the substituent into the uncoordinating aromatic compound constituting a stack structure in the three-dimensional lattice-like structure. By such high structural regularity of the channel group, the environmental characteristics of channels in each of the channel groups can be uniformly maintained in the polymer complex as a whole, and the polymer complex having such channel groups exhibits higher selectivity for guest components.

According to the present invention, therefore, the characteristics of channel environments of the channel groups formed in the polymer complex can be easily regulated according to the purpose by selecting the type, introducing position, number etc. of substituents A introduced into the uncoordinating aromatic compound, and therefore, the polymer complex that can be provided by the present invention, as compared with the polymer complex in Japanese Patent Application No. 2004-382152 supra, enables more selective separation of two or more components from a mixture, storage thereof in a separated state, or transportation thereof in a separated state, and more selective release of the components stored in the polymer complex. Further, when a channel space of the channel group in the polymer complex is utilized as a reaction field, the reaction field can be regulated precisely by regulation of channel characteristics, to realize high-degree control of chemical reaction, and as a result, highly selective material exchange can be achieved.

The three-dimensional coordination network also includes a complexed three-dimensional coordination network comprising two or more independent three-dimensional networks complexed with one another. This complexed three-dimensional coordination network includes, for example, an interpenetrated structure wherein independent three-dimensional coordination networks are intricately intertwined with one another.

Two channel groups selected arbitrarily from the two or more kinds of channel groups are made different from each other in respect of the affinity, for guest components, of channels constituting each of the channel groups by making them different in at least one factor selected from the size of a channel, the shape of a channel and the atmosphere in a channel in comparison therebetween.

When the stack structure is formed by stacking aromatic compound ligands and uncoordinating aromatic compounds sufficiently wherein the three-dimensional coordination network is formed with a sufficient three-dimensional extension, the resulting channels are in a long and thin form.

The size of a channel contained in a channel group selected from the two or more channel groups may be appropriately designed depending on a component intended to be selectively incorporated, released and/or transported. Specifically, the diameter of an inscribed circle of the channel can be 2 to 70 Å on a face parallel to a crystal plane most perpendicular to the direction in which the channel extends.

The major axis of an inscribed ellipse of a channel contained in a channel group selected from the two or more kinds of channel groups can be 5 to 70 Å, and the minor axis of the inscribed ellipse can be 2 to 50 Å, on a face parallel to a crystal plane most perpendicular to the direction in which the channel extends.

Specific examples of the aromatic compound ligand include aromatic compounds represented by the following formula (1):

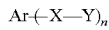

wherein Ar is a structure having an aromatic ring, X is a divalent organic group or a single bond through which Ar and Y are directly bound to each other, Y is a coordinating atom or a coordinating atom-containing atomic group, n is a number of 3 to 6, and a plurality of Xs contained in one molecule may be different from one another, and a plurality of Ys may be different from one another.

Specific examples of the uncoordinating aromatic compound include condensed polycyclic aromatic compounds.

More specifically, the polymer complex is a complex wherein the aromatic compound represented by the formula (1) is tris(4-pyridyl)triazine, and the condensed polycyclic aromatic compound is at least one member selected from triphenylene and perylene. In the polymer complex in this form, the diameter of an inscribed circle of a channel contained in a channel group selected from the two or more channel groups is specifically 4.5 to 7.0 Å on a face parallel to a crystal plane most perpendicular to the direction in which the channel extends. The major axis of an inscribed ellipse of a channel contained in a channel group selected from the two or more kinds of channel groups is 8.5 to 10.0 Å, and the minor axis of the inscribed ellipse is 6.0 to 8.0 Å, on a face parallel to a crystal plane most perpendicular to the direction in which the channel extends. The channel when having such a relatively large size can incorporate a guest component having a relatively large molecular size, such as an organic compound.

The substituent A is not particularly limited; for example, the substituent A is preferably one that can exhibit an intramolecular interaction higher than van der Waals' force in the polymer complex.

In the stack structure in the three-dimensional coordination network, by selecting the uncoordinating aromatic compound, a substituent to be introduced into the uncoordinating aromatic compound and the aromatic compound ligand so that the HOMO (highest occupied molecular orbital) of the uncoordinating aromatic compound and the LUMO (lowest unoccupied molecular orbital) of the aromatic compound ligand overlap in the number and position of nodal planes, in electron distribution, and in the orbital shape with respect to energy level and the stack structure to be stabilized, the stack structure to be formed in the polymer complex can be predicted and efficient molecular design is feasible.

By way of example, the substituent A is at least one functional group selected from —W—OH, —W—NH$_2$, —W—NO$_2$, —W—CH$_3$, —W—OCOCH$_3$, an alkyl ether chain, an alkylthio ether chain, an alkylene glycol chain, and a peptide chain, wherein W represents a divalent organic group or a single bond.

From the viewpoint of enabling construction of a stable three-dimensional structure by forming strong π-π stacking, the substituent A is preferably an electron-donating group, for example at least one functional group selected from —W—OH, —W—NH$_2$, —W—CH$_3$, and an alkyl ether chain, wherein W represents a divalent organic group or a single bond.

In order that a channel toward the substituent A is oriented exhibits an inclusion behavior, it is important that the channel is not occupied by the substituent A, and from this viewpoint, the substituent A is preferably an atomic group having 3 or less atoms in total excluding hydrogen atoms.

Effect of the Invention

The polymer complex of the present invention can freely control the characteristics of a channel formed in the polymer complex by introducing a substituent into an uncoordinating aromatic compound constituting the polymer complex. Accordingly, the polymer complex of the present invention, as compared with the polymer complex disclosed in Japanese Patent Application No. 2004-382152 filed for a patent application by some of the present inventors, can increase the difference in properties among channel groups formed in the polymer complex so that the specificity as a property of the channel group is high and/or the structural regularity of the channel group is high. Accordingly, the channel groups in the polymer complex of the present invention are highly selective for specific components, thus exhibiting, for example, high selectivity in separation and storage of specific components from a mixture and in release and transportation of the specific components incorporated into two or more kinds of channel groups in the polymer complex. The channel in the polymer complex of the present invention can also be utilized as an accurately regulated reaction field and also enables highly selective material exchange.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 2 is a view showing a crystal structure of the polymer complex 4 (FIG. 2A) and a periodic structure having tris(4-pyridyl)triazine and 1-hydroxytriphenylene alternately stacked therein (FIG. 2B).

FIG. 3 is a view showing a molecular orientation of tris(4-pyridyl)triazine, 1-hydroxytriphenylene and zinc iodide in a three-dimensional lattice-like structure of the polymer complex 4 and the orientation of methanol included in channel P.

FIG. 4 is a view which shows a molecular orientation of tris(4-pyridyl)triazine, 1-hydroxytriphenyleneand zinc iodide in a three-dimensional lattice-like structure of the polymer complex 4 and the orientation of methanol included in channel P, and which shows the stacking distance between tris(4-pyridyl)triazine and 1-hydroxytriphenylene and the distance between an oxygen atom of methanol and an oxygen atom of 1-hydroxytriphenylene.

FIG. 7 is a view showing the HOMO of 1-hydroxytriphenylene and the LUMO of tris(4-pyridyl)triazine (FIG. 7a) and a view showing stacking thereof (FIG. 7b).

FIG. 8 is a view showing the HOMO of 2-aminotriphenylene and the LUMO of tris(4-pyridyl)triazine (FIG. 8a) and a view showing stacking thereof (FIG. 8b).

FIG. 9 is a table showing crystallographic data on the polymer complex 4, obtained by X-ray crystal structure analysis.

FIG. 10 is a table showing coordinate data on atoms of the polymer complex 4, obtained by X-ray crystal structure analysis.

FIG. 11 is a table showing coordinate data on atoms of the polymer complex 4, obtained by X-ray crystal structure analysis.

FIG. 12 is a table showing coordinate data on atoms of the polymer complex 4, obtained by X-ray crystal structure analysis.

FIG. 13 is a table showing coordinate data on atoms of the polymer complex 4, obtained by X-ray crystal structure analysis.

FIG. 14 is a table showing coordinate data on atoms of the polymer complex 4, obtained by X-ray crystal structure analysis.

FIG. 15 is a table showing coordinate data on atoms of the polymer complex 4, obtained by X-ray crystal structure analysis.

FIG. 16 is a table showing coordinate data on atoms of the polymer complex 4, obtained by X-ray crystal structure analysis.

FIG. 17 is a table showing coordinate data on atoms of the polymer complex 4, obtained by X-ray crystal structure analysis.

FIG. 18 is a table showing coordinate data on atoms of the polymer complex 4, obtained by X-ray crystal structure analysis.

FIG. 19 is a table showing coordinate data on atoms of the polymer complex 4, obtained by X-ray crystal structure analysis.

FIG. 20 is a table showing coordinate data on atoms of the polymer complex 4, obtained by X-ray crystal structure analysis.

FIG. 21 is a table showing crystallographic data on polymer complex 3, obtained by X-ray crystal structure analysis.

FIG. 22 is a table showing coordinate data on atoms of the polymer complex 3, obtained by X-ray crystal structure analysis.

FIG. 23 is a table showing coordinate data on atoms of the polymer complex 3, obtained by X-ray crystal structure analysis.

FIG. 24 is a table showing coordinate data on atoms of the polymer complex 3, obtained by X-ray crystal structure analysis.

FIG. 25 is a table showing coordinate data on atoms of the polymer complex 3, obtained, by X-ray crystal structure analysis.

FIG. 26 is a table showing coordinate data on atoms of the polymer complex 3, obtained by X-ray crystal structure analysis.

FIG. 27 is a table showing coordinate data on atoms of the polymer complex 3, obtained by X-ray crystal structure analysis.

FIG. 28 is a table showing coordinate data on atoms of the polymer complex 3, obtained by X-ray crystal structure analysis.

FIG. 29 is a table showing coordinate data on atoms of the polymer complex 3, obtained by X-ray crystal structure analysis.

FIG. 30 is a table showing coordinate data on atoms of the polymer complex 3, obtained by X-ray crystal structure analysis.

FIG. 31 is a table showing coordinate data on atoms of the polymer complex 3, obtained by X-ray crystal structure analysis.

FIG. 32 is a table showing coordinate data on atoms of the polymer complex 3, obtained by X-ray crystal structure analysis.

FIG. 33 is a table showing coordinate data on atoms of the polymer complex 3, obtained by X-ray crystal structure analysis.

FIG. 34 is a table showing coordinate data on atoms of the polymer complex 3, obtained by X-ray crystal structure analysis.

FIG. 35 is a table showing coordinate data on atoms of the polymer complex 3, obtained by X-ray crystal structure analysis.

FIG. 36 is a table showing coordinate data on atoms of the polymer complex 3, obtained by X-ray crystal structure analysis.

FIG. 37 is a view showing a crystal structure after a guest exchange experiment of the polymer complexes 5 and 7.

BEST MODE FOR CARRYING OUT THE INVENTION

Figure 1:
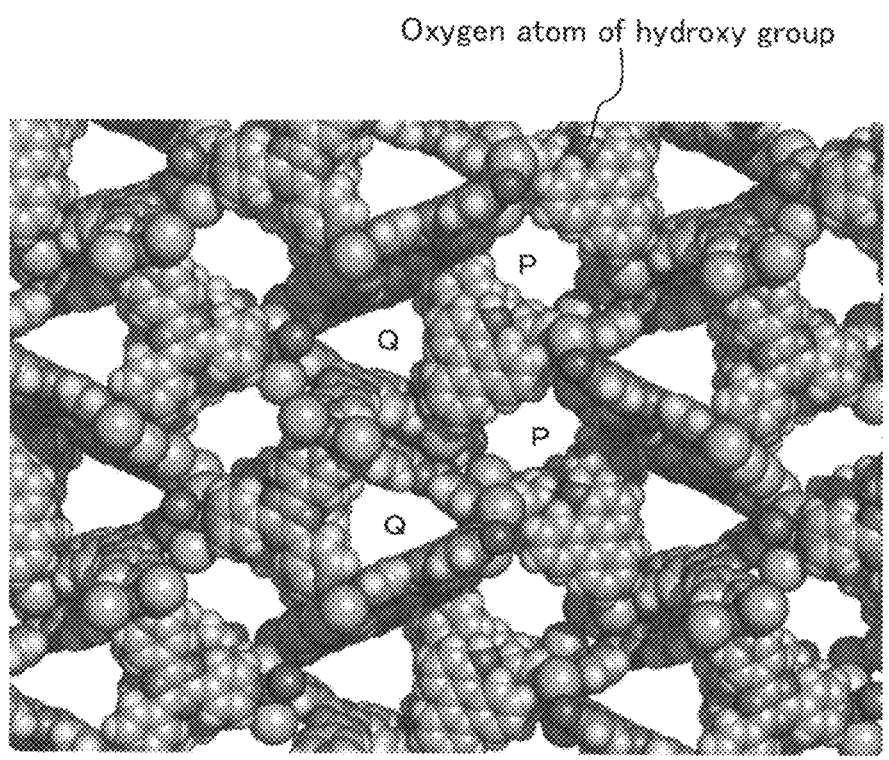
FIG. 1 is a projection view of the main framework of the polymer complex 4 drawn by using its van der Waals' radius, to show a method of calculating the channel size of the polymer complex 4.

The polymer complex of the present invention comprises an aromatic compound having two or more coordinating sites as a ligand, a metal ion as a central metal, and an uncoordinating aromatic compound, wherein the polymer complex has a three-dimensional lattice-like structure containing a stack structure comprising the uncoordinating aromatic compound intercalated between the aromatic compound ligands in a three-dimensional coordination network formed by coordinating the aromatic compound ligands to the central metal ion, the three-dimensional lattice-like structure is provided with two or more kinds of channel groups each composed of channels identical with one another and having inherent affinity for guest components, the uncoordinating aromatic compound has a specific substituent A at a specific position on the aromatic ring thereof, and the uncoordinating aromatic compound is arranged regularly such that the substituent A is directed to the inside of a specific channel group B out of the two or more kinds of channel groups.

The polymer complex of the present invention is a improvement to the polymer complex in Japanese Patent Application No. 2004-382152 filed by some of the present inventors, and similar to the polymer complex of Japanese Patent Application No. 2004-382152, has formed a three-dimensional coordination network by coordinate bonding of aromatic compound ligands to a central metal ion, and has a three-dimensional lattice-like structure containing a stack structure wherein an uncoordinating aromatic compound not involved in coordinate bonding is intercalated between aromatic compound ligands forming the three-dimensional coordination network. It is estimated that a plurality (that is, channel groups) of channels of two or more kinds each having inherent affinity for guest components (that is, having a specific molecular inclusion function) are formed in the polymer complex both from the three-dimensional coordination network by coordinate bonding of aromatic compound ligands to a central metal ion and from the stack structure formed by uncoordinating aromatic compounds incorporated into the three-dimensional coordination network and the aromatic compound ligands.

In the polymer complex in Japanese Patent Application No. 2004-382152, two or more kinds of channel groups compose of channels having inherent affinity for guest components, and each of the channel groups can, by this inherent affinity, incorporate a different guest component selectively. That is, the polymer complex can incorporate one or more kinds of guest components into each of two or more kinds of channel groups contained in one polymer complex, that is, the polymer complex as a whole can selectively incorporate two or more kinds of guest components. Further, the guest components incorporated into the channels can also be selectively released. Selective incorporation of the guest component into the channel and/or selective release thereof from the channel includes not only incorporation of a specific component into the channel and/or release of a specific component from the channel, depending on the atmosphere in the channel, the size and shape of the channel, etc. . . . but also selection of a guest component incorporated into the channel and/or a guest component released from the channel, depending the temperature condition, atmosphere and time for guest exchange.

By suitably regulating the size of channels contained in channel groups formed in the polymer complex, the polymer complex can incorporate, into the channels, compounds ranging from gaseous small molecules to large molecules such as proteins and other biomolecules. That is, each of the channel groups can selectively incorporate a specific compound from a mixture containing two or more kinds of small-molecule to large-molecule compounds.

Accordingly, the polymer complex can separate specific two or more components for example from a mixture containing two or more components and can store them in the polymer complex. From mixture 1 containing one or more components, a specific component only is incorporated into a channel in certain channel group 1, and while the component is maintained in the channel in channel group 1, another specific component from a mixture containing one or more components different from those of the mixture 1 can be incorporated into a channel in a certain channel group 2. Alternatively, when the polymer complex is used as a material constituting a partition wall, Compound a incorporated selectively into channel group A can be transported through the channel group A, while Compound b incorporated selectively into channel group B can be transported through the channel group B between the areas separated with the partition wall. At this time, when the compound is transferred according to the concentration distribution of each compound or temperature distribution, the transportation direction of Compound a may be the same as the transportation direction of Compound b, or the transportation direction of Compound a may be opposite to the transportation direction of Compound b.

Two or more kinds of guest components incorporated respectively into channel groups can be released separately under different conditions. For example, when the polymer complex having the guest components incorporated respectively into two or more kinds of channel groups is placed under a predetermined condition, the guest component to be released varies depending on the time for which the polymer complex is exposed to this condition. Specifically, when the polymer complex having different components incorporated respectively into the channel groups 1 and 2 is heated, the component incorporated into the channel contained in the channel group 1 is first released, and when heating is further continued, the component incorporated into the channel contained in the channel group 2 can be released.

For the sake of descriptive convenience, expressions such as mixture 1, channel group 1 etc. have been used to describe the action of the polymer complex, but the expressions such as mixture 1 etc. do not refer to a specific mixture, channel group etc.

The present inventors made extensive study, and as a result, they found that channels in channel groups formed in the polymer complex can be modified to further increase specificity in the inclusion function of the polymer complex by introducing substituents into aromatic rings of uncoordinating aromatic compounds constructing a stack structure in a three-dimensional lattice-like structure in the polymer complex together with aromatic compound ligands and forming an inner wall of a channel.

The detailed mechanism of the substituents introduced into aromatic rings of uncoordinating aromatic compounds is not completely elucidated, but it was found this time by the present inventors through research that the substituents are regularly oriented toward the inside of a channel in a specific channel group among the two or more kinds of channel groups. The orientation of the substituents is determined by a stabilization effect attributable to overlapping or orbital shape ($\pi$-$\pi$ interaction) such as an overlap between the nodal plane of the HOMO of the uncoordinating aromatic compound and the nodal plane of the LUMO of the aromatic compound ligand in the stack structure and an overlap in electron distribution, in addition to the interactions (for example, hydrogen bonding, ionic bonding, electrostatic interactions [dipole interaction, quadrupole coupling], and steric interaction) between the substituents and a specific channel group among the two or more kinds of channel groups. A part of the inner face of the specific channel group is constituted by the substituents, thereby the shape, size and atmosphere of the channel group significantly change. As a result, characteristics of the channel environment of the channel group, for example, acidity/basicity, hydrophilicity/hydrophobicity, polarity, chirality, fluidity etc. are simultaneously significantly changed, and the affinity of the channel group for a specific guest component is changed.

The environmental characteristics in the channel can be controlled at will according to the properties, number and size of the substituent introduced into an aromatic ring of the uncoordinating aromatic compound, or a combination of substituents when two or more substituents are to be introduced. For example, a guest component that cannot be incorporated into the polymer complex into which no substituent has been introduced according to Japanese Patent Application No. 2004-382152 can be incorporated into the polymer complex by introducing the substituents, or two or more guest components that cannot be separated from one another by only the channel atmosphere of each channel group in the polymer complex according to Japanese Patent Application No. 2004-382152 can be separated by the polymer complex wherein the shape or size of the channel is changed by introducing the substituents. Further, two or more kinds of channel groups can be made significantly different in channel environmental characteristics by regulating the type, number, introducing position etc. of substituents introduced to an aromatic ring of the uncoordinating aromatic compound, so that two or more guest components significantly different in characteristics can be incorporated into the respective channel groups, released and/or transported.

Specifically, when two channel groups different in hydrophobicity exist in the polymer complex comprising an uncoordinating aromatic compound into which no substituent is introduced, the introduction of substituent(s) into the uncoordinating aromatic compound can lead to (1) an increase in the hydrophilicity of one of the channel groups, (2) a decrease in the hydrophilicity of one of the channel groups, and (3) differentiation and improvement in hydrophilicity for each of the two channel groups. By increasing the difference in hydrophilicity of channels between the 2 channel groups according to (1) and (2), the affinity and specificity for the guest component can further be increased, and the ability to separate the guest component by incorporation or release thereof can be increased. A hydrophilic guest component that cannot be incorporated into a channel group constituted by the uncoordinating aromatic compound having no substituent introduced into it can be incorporated according to (3), and different guest components can be incorporated into the channel groups respectively. By introducing the substituents into the uncoordinating aromatic compound according to the present invention, a polymer complex having channels imparted every characteristic can be constructed to regulate not only the type, amount and arrangement of guest components incorporated into channels of the polymer complex, but also the reaction rate, reaction selectivity etc. of the guests, as described above. The polymer complex of the present invention is excellent in molecular design given many choices for the type, number and position of substituents.

The introduction of substituents into aromatic rings of the uncoordinating aromatic compounds brings about another effect of increasing the regularity in arrangement of the uncoordinating aromatic compounds in the polymer complex. As described above, the substituents introduced into the uncoordinating aromatic compounds are oriented toward the inside of a specific channel group out of the two or more channel groups, by physicochemical and/or steric interactions around the substituents, thereby conferring inherent characteristics on the channel environment. By such interactions, the regularity in arrangement of the uncoordinating aromatic compounds and aromatic compound ligands that are stacked with one another is increased, so the stack structure having the uncoordinating aromatic compounds and aromatic compound ligands stacked with one another is formed with regularity to form a strong structure.

By such high regularity of the stack structure, that is, by high structural regularity of the channel group, the environmental characteristics of channels in each of the channel groups can be uniformly maintained in the polymer complex. That is, it is meant that the selectivity of the channel group of the polymer complex for guest components is further increased.

In the present invention, the three-dimensional coordination network comprising aromatic compound ligands coordinated to a central metal also includes a complexed three-dimensional coordination network comprising, for example, two or more independent three-dimensional coordination networks complexed with one another preferably so as to have the same space in common. Specific examples of the complexed three-dimensional coordination network can include an interpenetrated structure comprising two or more independent three-dimensional coordination networks intricately intertwined with one another so as to have the same space in common.

In the present invention, the aromatic compound is a compound having at least one aromatic ring and may have a substituent or may contain an endocyclic heteroatom. The aromatic compound ligand used in the present invention is a multidentate aromatic compound having two or more coordinating sites. Preferably, the aromatic compound ligand is an aromatic compound wherein all coordinating sites constituting the aromatic compound ligand exist in almost the same plane. Particularly, the aromatic compound ligand when viewed as a whole is preferably in the form of a pseudo-plane owing to its π-conjugated system; that is, the aromatic compound ligand is an aromatic compound ligand, at least a part of the molecular structure of which becomes unified by the π-conjugated system to give rise to a stable pseudo-plane structure containing all coordinating sites therein.

By using the aromatic compounds having such a pseudo-plane structure as the ligand, the aromatic compounds are coordinated to a central metal ion to form a three-dimensional coordination network having higher regularity and rigidity. By increasing the regularity of the three-dimensional coordination network, a stack structure comprising the aromatic compound ligands and the uncoordinating aromatic compounds can be stably formed, and simultaneously channels and channel groups having higher regularity can be formed. In addition, a complexed three-dimensional coordination network having two or more independent three-dimensional coordination networks complexed with one another may be formed.

The three-dimensional coordination network has rigidity so that the stability, strength etc. of the three-dimensional lattice-like structure formed therefrom can be kept high. The three-dimensional coordination network has rigidity so that the strength of the resulting polymer complex is made relatively high to render it usable in applications requiring strength, thus broadening the technical range in which the polymer complex of the present invention can be used.

From the above viewpoint, the aromatic compound ligand that can be preferably used in the present invention includes, but is not limited to, an aromatic compound ligand having coordinating atoms arranged radially at regular intervals in the extending direction of a plane formed by the π-conjugated system of the aromatic ring as the center.

The uncoordinating aromatic compound used in the present invention is an aromatic compound present in the polymer complex by intercalating between the aromatic compound ligands through a bond or interaction other than coordinate bond, and does not form a coordinate bond in the polymer complex of the present invention. Accordingly, the uncoordinating aromatic compound as used herein may essentially have an ability to form a coordinate bond. Preferably, the uncoordinating aromatic compound is an aromatic compound in a molecule structure containing all aromatic rings unified in the π-conjugated system to have a stable pseudo-plane shape. By having the pseudo-plane shape, the uncoordinating aromatic compound can be easily intercalated between the aromatic compound ligands in a three-dimensional coordination network formed by the aromatic compound ligands, to form a stable structure having the aromatic compound ligand-uncoordinating aromatic compound-aromatic compound ligand stacked with one another.

When the aromatic compound ligand has also a pseudo-plane shape, the plane of the aromatic compound ligand and the plane of the uncoordinating aromatic compound are opposed to each other and stacked with each other thus allowing the π-π interaction to act on between the aromatic compound ligand-uncoordinating aromatic compound-aromatic compound ligand. As a result, the uncoordinating aromatic compound though having no direct bond to the aromatic compound ligand can be firmly confined between the aromatic compound ligands to form a more stable three-dimensional lattice-like structure.

The uncoordinating aromatic compound thus confined firmly between the aromatic compound ligands will not be extracted even under general guest exchange conditions with an aromatic compound as a guest component. Accordingly, the three-dimensional lattice-like structure having a stack structure in which the uncoordinating aromatic compound confined firmly between the aromatic compound ligands can be kept without changing its structure before and after guest components incorporated into the channels in the three-dimensional lattice-like structure are exchanged with other guest components.

A remarkable feature of the polymer complex of the present invention lies in that the uncoordinating aromatic compound has the specific substituent A at a specific position of the aromatic ring thereof. The substituent A refers to a certain atom or atomic group substituted in place of a hydrogen atom at a specific position of the aromatic ring of the uncoordinating aromatic compound.

The substituent A can be selected appropriately to bring about desired environmental characteristics in a channel of channel group B and is not particularly limited as long as it can be introduced into specific channel group B out of the two or more kinds of channel groups formed in the polymer complex having the uncoordinating aromatic compound as an constituent element. The number of substituents A possessed by the uncoordinating aromatic compound may be 1 or 2 or more. When two or more substituents A are to be introduced, the substituents A may consist of one kind of substituent or a combination of two or more kinds of substituents. The position of the substituent A on the aromatic ring of the uncoordinating aromatic compound is not particularly limited, and a plurality of substituents A may be introduced so as to face the inside of channels of one kind of channel group or may be introduced so as to face respectively the inside of channels of two or more channel groups.

The stack structure comprising the uncoordinating aromatic compound intercalated between the aromatic compound ligands may have at least one unit consisting of the uncoordinating aromatic compound intercalated between the aromatic compound ligands, but preferably has a structure having the aromatic compound ligand and the uncoordinating aromatic compound stacked alternately with each other to a certain extent. In polymer complex 4 described later, this stack structure is infinitely continued, but may not infinitely continued as long as the number of stacking units is sufficient for formation of two or more kinds of channel groups.

When the sufficiently three-dimensionally extending three-dimensional coordination network having the aromatic compound ligands coordinated to the metal ion, and the stack structure having the aromatic compound ligand and the uncoordinating aromatic compound stacked sufficiently with each other are formed, channels are formed in a long and thin form.

The two or more kinds of channel groups in the polymer complex are made different from one another in respect of their affinity for guest components by making them different in at least one factor selected from the size of a channel, the shape of a channel and the atmosphere in a channel, in comparison between two channel groups selected arbitrarily from the two or more kinds of channel groups. For increasing the affinity, for a specific guest component, of channels constituting each channel group in order to allow the channels to more selectively incorporate the specific guest component, it is preferable that 2 channel groups selected arbitrarily from the two or more kinds of channel groups are made different from each other in two or more factors selected from the size of a channel, the shape of a channel and the atmosphere in a channel, in comparison therebetween. Particularly, a channel group different from other channel groups in all the three factors (that is, the size of a channel, the shape of a channel and the atmosphere in a channel) is preferable because of higher selectivity for guest components.

A factor causing the atmosphere in channels to be made different among the channel groups is not particularly limited as long as the atmosphere in channels is thereby made different and the affinity for guest components is made different, and there are a variety of such factors depending on the properties of each guest component (for example, polarity etc.). The atmosphere in channels is significantly varied depending on characteristics of the substituent introduced into the uncoordinating aromatic compound. The atmosphere in channels is varied not only by the modification to channels attributable to characteristics of the substituent but also by a different ratio of the region over which the π-plane of aromatic compounds (aromatic compound ligands and/or uncoordinating aromatic compounds) constituting a wall forming a channel is exposed to an inner face of the wall, to the region over which hydrogen atoms of the aromatic compounds are exposed to the inner face of the wall.

When the size of the channel varies among the channel groups, the type of a guest component incorporated into the channel constituting each channel group and the amount of the guest component incorporated vary depending on the molecular size of the guest component. The size of the channel even in a continuous form varies depending on the position thereof on the polymer complex; that is, the minimum size of the channel significantly influences the minimum molecular size of the guest component that can be incorporated into the channel, while the maximum size of the channel significantly influences the maximum molecular size of the guest component that can be incorporated into the channel and the amount of the guest component that can be incorporated. Accordingly, the size of the channel is an important factor influencing the affinity thereof for the guest component.

The channel formed in the three-dimensional lattice-like structure of the polymer complex meanders locally to some extent, but when the three-dimensional lattice-like structure is viewed as a whole, the channel extends in a predetermined direction with directionality. Accordingly, the diameter of an inscribed circle of the channel on a parallel face to a crystal plane most perpendicular to the direction in which the channel extends can be an indicator of channel size. The direction in which the channel extends is the direction of the channel that is regarded as one continuous void as a whole by disregarding local meandering thereof.

Figure 6:
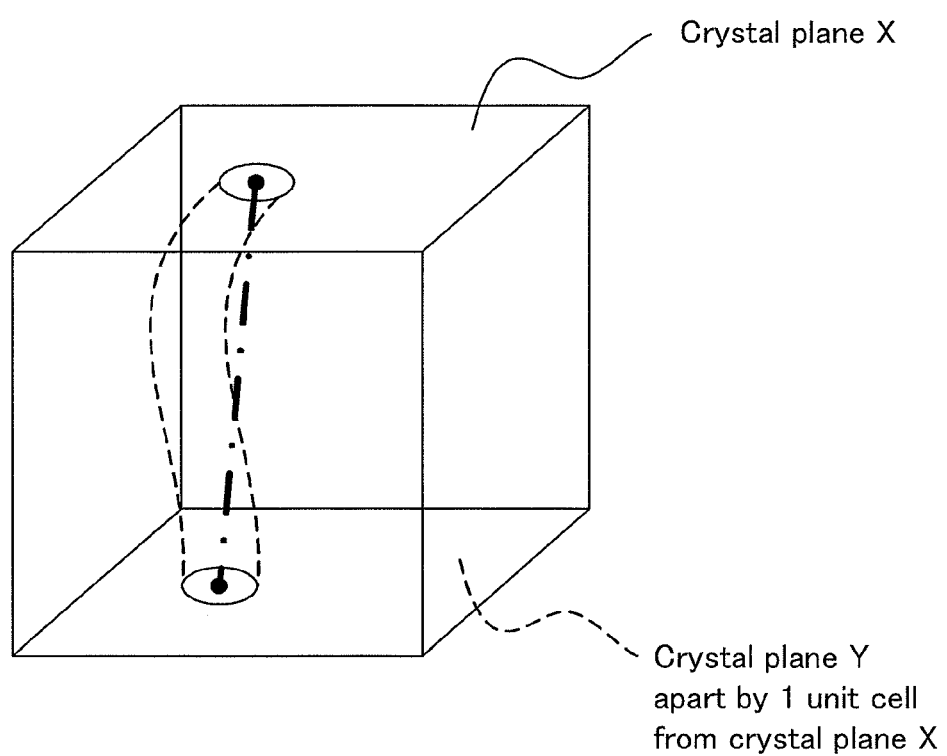
FIG. 6 is a view showing a method of determining the direction in which the channel extends.

The direction in which the channel extends can be determined for example as follows. Crystal plane X (plane A, plane B, plane C or its diagonal plane) in a suitable direction across the channel whose size is to be measured, and crystal plane Y placed apart by 1 unit cell from the crystal plane X, are selected, and sectional views of the channel on the respective crystal planes X and Y are drawn. Then, a straight line (alternate long and short dash line) is drawn from the center of the section of the channel on one crystal plane to the center of the section thereof on another crystal plane (see FIG. 6). The direction of the straight line thus obtained agrees with the direction in which the channel extends. Then, a crystal plane that intersects with the obtained straight line at the nearest angle to 90° is selected, and the diameter of an inscribed circle of the channel on this crystal plane can be regarded as the size of the channel.

If the size of the channel is assumed to be a sole factor that determines the selectivity of the channel for guest components, a guest component having a smaller molecular size than the diameter of an inscribed circle of the channel can usually be incorporated into the channel without difficulty, and thus the definition of channel size in terms of the diameter of the inscribed circle thereof has a significant meaning. The channel groups may be different from one another in channel size, and there is no limitation to the difference in channel size, etc., among the channels groups.

The size of the channel to be formed in the polymer complex of the present invention may be appropriately designed depending on a component desired to be selectively incorporated, and the channel can, depending on its size, incorporate compounds ranging from gaseous small molecules to large molecules such as proteins and other biomolecules. Specifically, the diameter of the inscribed circle can be 2 to 70 Å, preferably 2 to 20 Å. Alternatively, the major axis of an inscribed ellipse of the channel on the parallel face can be 5 to 70 Å, and the minor axis of an inscribed ellipse of the channel can be 2 to 50 Å. When the channel sizes of the respective channel groups are different, the channel sizes of the respective channel groups are different from one another preferably in the range defined above.

It is preferable that as factors to be compared among the different channel groups, the minor and major axes of an inscribed ellipse of the channel, together with the diameter of an inscribed circle of the channel, are considered as measures for specifying the deviation of the channel shape from the inscribed circle.

Now, the method for measurement (calculation) of the size of a channel is described by reference to FIG. 1. FIG. 1 is a projection view, on crystal plane (010), of a main backbone of polymer complex 4 (described later) drawn by using its van der Waals' radius, wherein guest components incorporated into channels P and Q are not shown.

In the polymer complex 4, the channels P and Q extend in a direction (which is not a local direction but an overall direction as described above) perpendicular to the crystal plane (010), that is, in a direction perpendicular to the plane of page of FIG. 1. Because the plane of page of FIG. 1 is the parallel plane described above, the diameter of an inscribed circle of the channel shown in FIG. 1 and/or the major and minor axes of an inscribed ellipse thereof are measured, and these measures can be reduced to the actual size of the channel.

The size of the channel can be regulated by molecular design, for example, by designing the molecular size of the aromatic compound ligand or uncoordinating aromatic compound constituting the three-dimensional lattice-like structure, the coordination force between the central metal ion and the aromatic compound ligand, and the type, number and position of substituents introduced into the uncoordinating aromatic compound.

When the channel groups are different in channel shape, the guest component that can be incorporated into channels constituting each channel group varies depending on the shape of the guest component, even if the channel groups are almost identical in the diameter of the inscribed circle or in the major and minor axes of the inscribed ellipse. The channels constituting each channel group may be different in channel shape at least in one position and may not be different in the whole of a continuous channel.

The shape of the channel can also be regulated by molecular design, for example, by designing the shape of the aromatic compound ligand or uncoordinating aromatic compound constituting the three-dimensional lattice-like structure, and the type, number and position of substituents introduced into the uncoordinating aromatic compound.

In the stack structure in the three-dimensional coordination network, by selecting the uncoordinating aromatic compound, a substituent to be introduced into the uncoordinating aromatic compound and the aromatic compound ligand so that the HOMO (highest occupied molecular orbital) of the uncoordinating aromatic compound and the LUMO (lowest unoccupied molecular orbital) of the aromatic compound ligand overlap in the number and position of nodal planes, in electron distribution, and in the orbital shape with respect to energy level (see FIG. 7(b) and FIG. 8(b)) and the stack structure to be stabilized, the stack structure to be formed in the polymer complex can be predicted and efficient molecular design is feasible.

Hereinafter, the aromatic compound ligand, the uncoordinating aromatic compound and the metal ion as a central metal, which constitute the polymer complex of the present invention, are specifically described.

Specific examples of the aromatic compound ligand include, for example, aromatic compounds represented by the following formula (1):

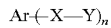

wherein Ar is a structure having an aromatic ring, X is a divalent organic group or a single bond through which Ar and Y are directly bound to each other, Y is a coordinating atom or a coordinating atom-containing atomic group, n is a number of 3 to 6, and a plurality of Xs contained in one molecule may be different from one another, and a plurality of Ys may be different from one another.

In the formula (1), Ar has a π plane forming a pseudo-plane structure and has a π-π interaction with the uncoordinating aromatic compound. Ar is not particularly limited and may be appropriately selected by considering a certain influence of the molecular size of the aromatic compound ligand on the size of a channel to be formed in the polymer complex. Specific examples of Ar include a monocyclic aromatic ring, particularly a 6-membered aromatic ring of a condensed polycyclic aromatic ring bi- to pentacyclic, particularly a condensed polycyclic aromatic ring having two to five 6-membered aromatic rings condensed therein.

For easiness in synthesis, Ar is preferably a monocyclic aromatic ring such as a 6-membered aromatic ring. Examples of the monocyclic 6-membered aromatic ring include a benzene ring, a triazine ring, a pyridine ring, a pyrazine ring etc. Ar may be a structure having an aromatic ring, and may partially contain an alicyclic cyclic structure or an endocyclic heteroatom. Ar may have a substituent other than —(X—Y).

When X intermediating between Ar and Y in the formula (1) is a divalent organic group, its chain length etc. may be selected appropriately depending on the required size etc. of a channel formed in the polymer complex. For forming a channel that can incorporate an organic compound having a relatively large molecular size, examples of X include a divalent aliphatic group having 2 to 6 carbon atoms, a 6-membered divalent monocyclic aromatic ring, and a condensed polycyclic aromatic ring having two to four 6-membered aromatic rings.

The aromatic ring may contain an endocyclic hetero atom or may have a substituent. The aromatic ring may partially contain an alicyclic structure. The alicyclic group may have a branched structure, may contain an unsaturated bond, or may contain a heteroatom.

Specific examples of the divalent organic group includes a monocyclic aromatic ring such as a phenylene group, thiophenylene, or furanylene, a condensed polycyclic aromatic ring having benzene rings condensed therein, such as a naphthyl group or anthracene, an aliphatic group such as an acetylene group, an ethylene group, an amido group, or an ester group, and a group wherein these groups, the number of which is arbitrary, are linked to one another in an arbitrary order. A plurality of Xs contained in one molecule may be the same or different from one another, but is usually preferably the same from the viewpoint of easy synthesis.

Y is a coordinating atom, or a coordinating atom-containing atomic group, which can be coordinated to a central metal ion serving as a central metal, and is not particularly limited as long as it can be coordinated to the central metal ion to form a three-dimensional coordination network. Examples of Y include groups represented by the following formulae (2):

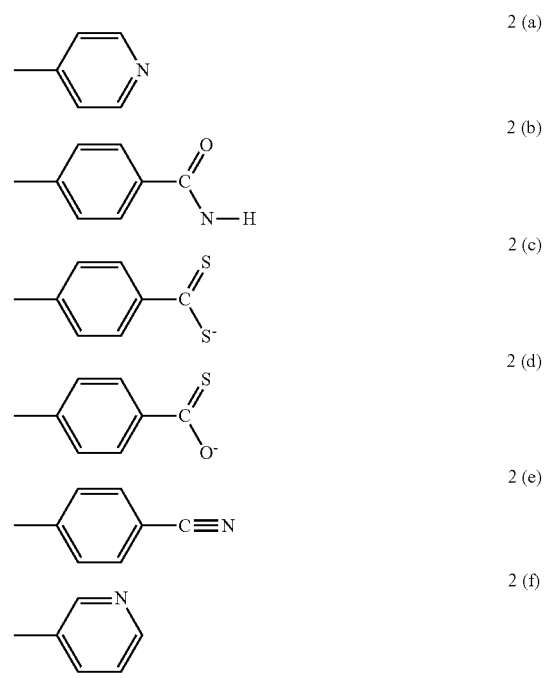

The formulae (2b), (2c) and (2d) have a resonance structure so that a lone electron pair can be given to the central metal ion. Hereinafter, the resonance structure of the formula (2c) is shown as a typical example.

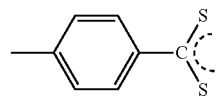

Y may be a coordinating atom itself or may be an atomic group containing a coordinating atom. For example, the above-mentioned 4-pyridyl group (2a) is an atomic group containing a coordinating atom (N). From the viewpoint of attaining suitable coordination strength upon coordination bonding to the central metal ion via a lone electron pair possessed by the coordinating atom of Y, the pyridyl group (2a, 2f) is particularly preferable among the groups of the above formulae.

A plurality of Ys contained in one molecule may be the same or different from one another.

As described above, the aromatic compound ligand is preferably an aromatic compound wherein all coordinating sites constituting the aromatic compound ligand exist in almost the same plane. Particularly, the aromatic compound ligand when viewed as a whole is preferably in the form of a pseudo-plane owing to its π-conjugated system. That is, all Ys contained in the aromatic compound ligand (1) represented by the formula (1) above are present preferably in almost the same plane. Particularly, a plurality of —(X—Y) bound to Ar become unified by the π-conjugated system to form a stable pseudo-plane structure in which all Ys exist.

From the viewpoint of exhibiting an effective π-π interaction with the uncoordinating aromatic compound, it is preferable that in the aromatic compound ligand wherein Ar and a plurality of —(X—Y) become unified by the π-conjugated system to form a stable pseudo-plane structure, —(X—Y) has a rigid linear structure, and in an environment intended to be used, its rotation on the axis is restricted.

From this viewpoint, preferable examples of X among those mentioned above include a single bond through which Ar and Y are directly bound to each other, an aromatic group, for example a monocyclic aromatic ring such as a phenylene group or a condensed polycyclic aromatic ring such as a naphthyl group or anthracene, an aliphatic group such as an acetylene group or an ethylene group, and a group wherein these groups, the number of which is arbitrary, are linked to one another in an arbitrary order. When —(X—Y) is a structure composing of an aromatic ring, an acetylene group or an ethylene group or a structure having these groups linked therein, its axial rotation is restricted due to steric hindrance. When the structure composing of an aromatic ring, an acetylene group or an ethylene group forms a conjugated system where π electrons are delocalized, its axial rotation is restricted by an energy barrier of the conformation. Accordingly, the aromatic compound ligands represented by the formula (1) can become unified to attain a pseudo-plane structure, to form a stable three-dimensional coordination network.

From the viewpoint of ease in design of the polymer complex, the coordinating atom represented by Y or the coordinating atom contained in Y preferably has a lone electron pair in the extending direction of the axis of —(X—Y) having the rigid linear structure described above.

The number of —(X—Y) bound to Ar is usually 3 to 6, depending on the structure of Ar. —(X—Y) is bound to Ar preferably such that its coordinating atoms are arranged radially at regular intervals in almost the same plate with Ar as the center.

The aromatic compound ligand (1) having a structure wherein coordinating atoms are arranged radially at regular intervals in the extending direction of a plane formed by the π-conjugated system of the aromatic ring with the aromatic ring-containing structure Ar as the center as described above includes aromatic compound ligands represented by the following formula (4):

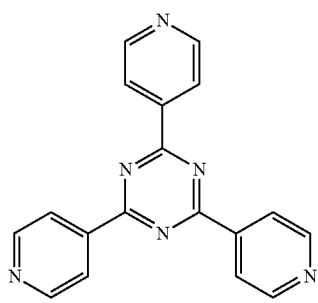

4 (a)

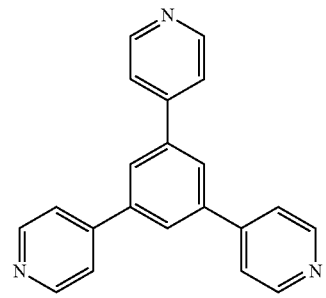

4 (b)

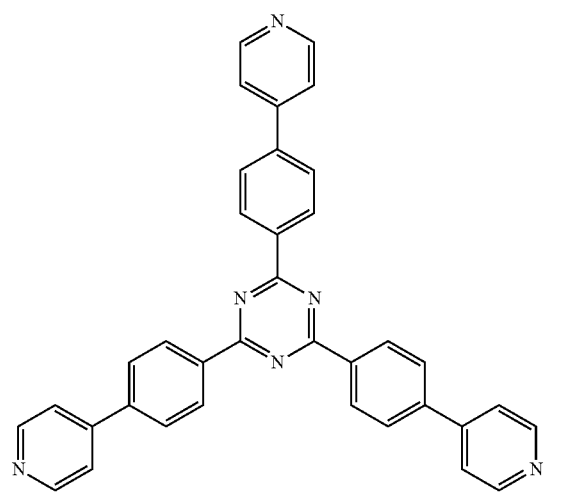

4 (c)

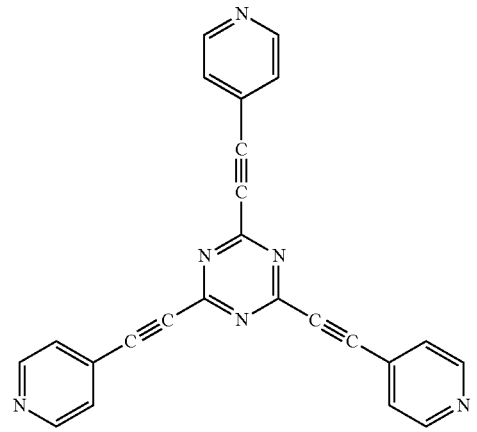

4 (d)

Among compounds in the formula (4) above, tris(4-pyridyl)triazine (4a) [2,4,6-tris(4-pyridyl) 1,3,5-triazine] is particularly preferable because it is deficient in electron and thus has strong interaction attributable to charge transfer with the uncoordinating aromatic compound so that a strongly stabilized stack structure with the uncoordinating aromatic compound can be formed.

As the uncoordinating aromatic compound, on the other hand, a condensed polycyclic aromatic compound can be mentioned. This is because for the reason described above, the uncoordinating aromatic compound is preferably an aromatic compound in a molecular structure containing all rings unified by the π-conjugated system to have a stable pseudo-plane shape.

The condensed polycyclic aromatic compound includes a bicyclic to heptacyclic compound. For stabilizing the stack structure with the aromatic compound ligands, the condensed polycyclic aromatic compound preferably has a planar shape extending to a certain extent. Such condensed polycyclic aromatic compound includes compounds represented by the following formula (5):

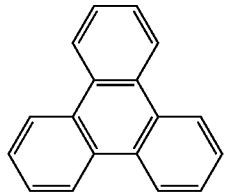

5 (a)

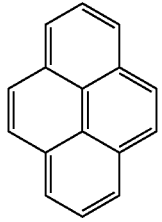

5 (b)

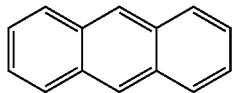

5 (c)

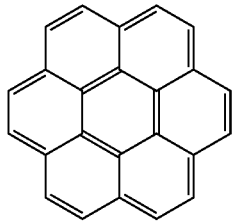

5 (d)

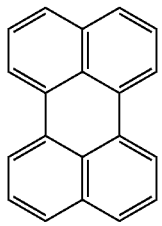

5 (e)

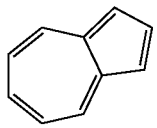

5 (f)

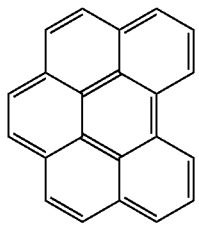

5 (g)

-continued

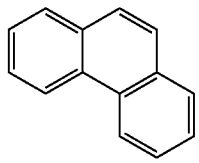

5 (h)

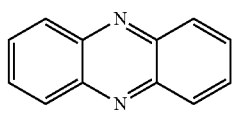

5 (i)

The substituent A introduced into the aromatic ring of the uncoordinating aromatic compound is not particularly limited as long as it has such a size as to permit the substituent A to enter into a channel formed in the polymer complex. Accordingly, the substituent A attaining the effect of substituent introduction varies depending on the size of a channel formed in the polymer complex. For example, the substituent A includes at least one functional group selected from —W—OH, —W—NH$_2$, —W—CH$_3$, —W—OCOCH$_3$, an alkyl ether chain, an alkylthio ether chain, an alkylene glycol chain, and a peptide chain, wherein W represents a divalent organic group or a single bond.

Although the divalent organic group W is not particularly limited as long as the obtained substituent A has such a size as to permit it to enter into the specific channel B, the divalent organic group W is preferably a lower carbon chain, specifically a carbon chain having 1 to 5 carbon atoms or a single bond, particularly preferably a carbon chain having 1 to 3 carbon atoms or a single bond. An alkyl or alkylene group of the alkyl ether, alkyl thio ether, or alkylene glycol is preferably a lower carbon chain, specifically a carbon chain having 1 to 5 carbon atoms, particularly preferably a carbon chain having 1 to 3 carbon atoms. The alkylene glycol chain or the peptide chain is preferably a chain containing 1 to 2 alkylene glycol or peptide units.

Specific substituent A can be exemplified by —CH$_2$—OH, —CH$_2$CH$_2$—OH, —OH, —CH$_2$—NH$_2$, —CH$_2$CH$_2$—NH$_2$, —NH$_2$, —CH$_2$—NO$_2$, —CH$_2$CH$_2$—NO$_2$, —NO$_2$, —CH$_2$—CH$_3$, —CH$_2$CH$_2$—CH$_3$, —CH$_3$, —CH$_2$—OCOCH$_3$, —CH$_2$CH$_2$—OCOCH$_3$, —OCOCH$_3$, —O—CH$_3$, —O—CH$_2$CH$_3$, —S—CH$_3$, —S—CH$_2$CH$_3$, and —O—CH$_2$CH$_2$—OH.

Substituents having relatively strong interactions such as hydrogen bonding, ionic bonding, electrostatic interactions (dipole interaction, quadrupole coupling) can be selected to regulate the orientation of the substituents and the arrangement of the uncoordinating aromatic compounds. Substituents that can exhibit higher interatomic or intermolecular interactions such as electrostatic interactions and steric effects than van der Waals' force can be introduced into aromatic rings of the uncoordinating aromatic compounds, whereby the molecular arrangement, by self-assembly, of the aromatic compound ligands and the uncoordinating aromatic compounds is more accurately regulated, and the orientation of the substituents themselves and the regularity of the stack structure composing of the aromatic compound ligand and the uncoordinating aromatic compound can be increased, in the three-dimensional coordination network formed by coordinating the aromatic compounds ligand to metal ions.

Among those described above, the substituents exhibiting relatively strong interactions described above includes —CH$_2$—OH, —CH$_2$CH$_2$—OH, —OH, —CH$_2$—NH$_2$, —CH₂CH₂—NH₂, —NH₂, —CH₂—NO₂, —CH₂CH₂—NO₂, —NO₂, —CH₂—OCOCH₃, —CH₂CH₂—OCOCH₃, —OCOCH₃, and —O—CH₂CH₂—OH.

From the viewpoint of constructing a stable network structure by forming a strong π-π stacking structure, the substituent A is preferably a highly electron-donating substituent. The highly electron-donating substituent includes —W—OH, —W—NH₂, —W—CH₃, and an alkyl ether chain, and specific examples include —CH₂—OH, —CH₂CH₂—OH, —OH, —CH₂—NH₂, —CH₂CH₂—NH₂, —NH₂, —CH₂—CH₃, —CH₂CH₂—CH₃, —CH₃, —O—CH₃, and —O—CH₂CH₃.

It is important that the channel containing the substituents A oriented toward the inner face thereof is not occupied by the substituents A in order to incorporate a guest component, that is, to exhibit an inclusion behavior. From this viewpoint, the size of the substituent A is preferably determined so as to be adapted to the size of the channel. Because the size of a space in the channel toward which the substituents A are oriented also varies depending on the size of the substituents A, the size of the substituents A can be determined so as to be adapted to the guest component intended to be incorporated.

Accordingly, the size of the preferable substituent A varies depending on the size of the channel and the size of the guest component intended to be included, but from the viewpoint of forming the channel showing an inclusion behavior, the substituent A is preferably an atomic group having 3 or less atoms in total excluding hydrogen atoms. Specifically, the above-mentioned W is preferably a carbon chain having 1 to 2 carbon atoms or a single bond, and when an alkyl ether chain is selected as the substituent A, W is preferably a carbon chain having 1 to 2 carbon atoms. Examples of such substituent A include —CH₂—OH, —CH₂CH₂—OH, —OH, —CH₂—NH₂, —CH₂CH₂—NH₂, —NH₂, —NO₂, —CH₂—CH₃, —CH₂CH₂—CH₃, —CH₃, —OCOCH₃, —O—CH₃, —O—CH₂CH₃, —S—CH₃, and —S—CH₂CH₃

The number of substituents introduced into the uncoordinating aromatic compound is not limited either, and may be 1 or 2 or more. When two or more substituents are introduced, the substituents may be the same or different from one another. Depending on the number of substituents introduced, the shape, size and atmosphere of the channel can be regulated as described above.

The position of the substituent introduced into the aromatic ring of the uncoordinating aromatic compound is not particularly limited. Depending on the position of the substituent introduced, the shape and size of the channel are changed, and the orientation of the substituent itself may also be changed by the steric effect. When a plurality of substituents are introduced into the uncoordinating aromatic compound, the plurality of substituents can, by the positions of the respective substituents introduced, be directed toward the same channel to modify one channel group with the plurality of substituents, or directed toward different channels to modify different channel groups with the respective substituents.

As the central metal ion to which the aromatic compound ligands are coordinated, various metal ions may be appropriately selected and used, among which transition metal ions are preferable. The transition metal in the present invention encompasses zinc, cadmium and mercury in the XII group in the periodic table. Particularly, the VIII to XII group elements are preferable, and specifically zinc, copper, nickel, cobalt, iron, silver etc. are preferable.

In the present invention, the central metal ion exists usually in the form of a compound such as a metal salt in the three-dimensional lattice-like structure. Metal compound containing these central metal ions include metal halide salts, and specifically, ZnI₂, ZnCl₂, ZnBr₂, NiI₂, NiCl₂, NiBr₂, CoI₂, CoCl₂, and CoBr₂ etc. are preferably used.

When the aromatic compound of the formula (1), particularly the aromatic compound of the formula (4), is used as the aromatic compound ligand, and a condensed polycyclic aromatic compound, particularly the aromatic compound of the formula (5) is used as the uncoordinating aromatic compound, the size of a channel contained in a channel group selected from the two or more kinds of channel groups formed in the polymer complex can be as follows: the diameter of the inscribed circle in the parallel plane mentioned above is in the range of 3 to 10 Å, particularly 4.5 to 7.0 Å, the major axis of the inscribed ellipse on the parallel plane is in the range of 5 to 15 Å, particularly 8.5 to 10.0 Å, and the minor axis of the inscribed ellipse on the parallel plane is in the range of 3 to 13 Å, particularly 6.0 to 8.0 Å. The polymer complex in which channels of such sizes are formed can incorporate compounds of relatively large sizes, such as organic compounds.

Now, the process for producing the polymer complex of the present invention, and the structure of the polymer complex, are described in more detail by reference to the polymer complex obtained by using tris(4-pyridyl)triazine (formula 4a) as the aromatic compound ligand, triphenylene having an —OH group introduced at position 1 (1-hydroxytriphenylene) (B₄ in the formula 6) as the uncoordinating aromatic compound, and ZnI₂ as a metal compound containing a metal ion as the central atom.

In formula (6) below, tris(4-pyridyl)triazine (A) is a compound having a pseudo-plane structure having a triazine ring and three pyridyl rings on almost the same plane, and three 4-pyridyl nitrogen atoms can be coordinated to a metal ion. 1-Hydroxytriphenylene (B₄) is also a compound having a pseudo-plane structure, and a hydroxyl group (—OH) is bound to an aromatic ring of the triphenylene skeleton thereof. The polymer complex having a three-dimensional lattice-like structure formed from tris(4-pyridyl)triazine (A) (hereinafter referred sometimes in the following formula to as (A)), ZnI₂, and 1-hydroxytriphenylene (B₄) (hereinafter referred sometimes in the following formula to as (B₄)) is formed by allowing tris(4-pyridyl)triazine (A) and 1-hydroxytriphenylene (B₄) in a coexisting state to act on ZnI₂ (Formula 6).

[Formula 6]

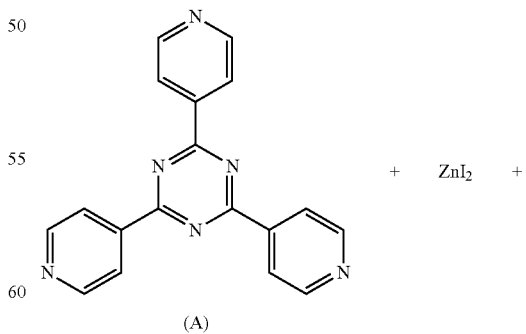

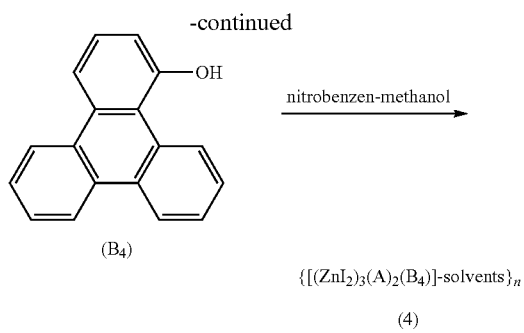

(B₄)

→ nitrobenzen-methanol

{[(ZnI$_2$)$_3$(A)$_2$(B$_4$)]-solvents}$_n$ (4)

For example, a polymer complex (hereinafter referred to sometimes as polymer complex 4) having a single-crystal structure represented by {[(ZnI$_2$)$_3$(A)$_2$(B$_4$)] (nitrobenzene)$_4$ (methanol)$_n$}$_z$ (n, z: nonstoichiometric composition)) can be produced by using a triple-layered solution (a top layer: a solution of ZnI$_2$ in methanol, a middle layer: methanol, a bottom layer: a solution of tris(4-pyridyl)triazine and 1-hydroxytriphenylene in nitrobenzene-methanol). At this time, the middle layer that is a methanol layer is a buffer for preventing ZnI$_2$ from being rapidly mixed with tris(4-pyridyl)triazine and 1-hydroxytriphenylene. By being left this triple-layered solution, ZnI$_2$ is mixed gradually with tris(4-pyridyl)triazine and 1-hydroxytriphenylene (double-layer diffusion method), thereby forming polymer complex 4.

FIG. 2 is a view of the polymer complex 4, which was obtained by X-ray crystal structure analysis. FIG. 2(A) with an axis b in a direction perpendicular to the plane of this figure (crystal 010 plane) shows an interpenetrated structure in the three-dimensional lattice-like structure of the polymer complex 4 on a plane of section perpendicular to the direction (axis b) in which channels P and Q (described later) extend. In FIG. 2(A), guest components incorporated into channels P and Q are not shown.

When the polymer complex 4 was analyzed by X-ray crystal structure analysis, it was found that the polymer complex 4 has a complexed three-dimensional coordination network formed by interpenetration of three-dimensional coordination networks 1a and 1b each having a plurality of tris(4-pyridyl)triazine and ZnI$_2$ bound three-dimensionally to each other via coordinate bonding. At this time, the three-dimensional coordination network 1a and the three-dimensional coordination network 1b do not have a direct or indirect bond via which both the networks have ZnI$_2$ in common, and the two networks are independent of each other and are interpenetrated to each other so as to have the same space in common.

According to X-ray crystal structure analysis, 1-hydroxytriphenylene (B$_4$) is intercalated firmly between the π-plane of tris(4-pyridyl)triazine (Aa) in the three-dimensional coordination network 1a and the π-plane of tris(4-pyridyl)triazine (Ab) in the three-dimensional coordination network 1b (see FIG. 2(B)). At this time, 1-hydroxytriphenylene (B$_4$) is incorporated between tris(4-pyridyl)triazines (Aa) and (Ab) via the π-π interaction between (Aa) and (Ab) and does not have a direct bond to tris(4-pyridyl)triazine. However, it is estimated that the solid-state structure of the polymer complex 4 is stabilized by a structure composing of an infinite number of continuing stack structures having triphenylene intercalated between the π-planes of two tris(4-pyridyl)triazines (‥Aa‥B$_4$‥Ab‥B$_4$‥). Because triphenylene was not extracted in a guest exchange experiment of the polymer complex consisting of tris(4-pyridyl)triazine, triphenylene and ZnI$_2$ in Japanese Patent Application No. 2004-382152, it is estimated that 1-hydroxytriphenylene (B$_4$) also functions as a part of the main framework of the polymer complex 4.

This firm confinement of 1-hydroxytriphenylene (B$_4$) is ascribed to charge-transfer (CT) interaction among Aa-B$_4$-Ab. In addition, calculation predicted that the HOMO (highest occupied molecular orbital) of 1-hydroxytriphenylene (B$_4$) and the LUMO (lowest unoccupied molecular orbital) of tris(4-pyridyl)triazine (A) have a suitable overlapping orbital shape with respect to nodal planes, electron distribution and energy level (see FIG. 7(a) and FIG. 7(b)). For convenience of theoretical calculation for this result, the LUMO of molecule A not forming the complex was handled as a model of LUMO of A in the framework of the polymer complex 4.

In the polymer complex 4, two kinds of channels (P and Q) arranged regularly in the three-dimensional lattice-like structure thereof exist as shown in FIG. 2. The channels P and Q are formed regularly between stack structures having tris(4-pyridyl)triazine (A) and 1-hydroxytriphenylene (B$_4$) stacked alternately with one another. The channel P is almost cylindrical and mainly surrounded by hydrogen atoms on the edge of the π-plane of infinitely stacked tris(4-pyridyl)triazine (A) and 1-hydroxytriphenylene (B$_4$). The hydroxy group of 1-hydroxytriphenylene (B$_4$) is directed to an inner face of channel P to form a part of the inner face of channel P. Accordingly, the channel P is modified with the hydroxy group, thus attaining higher hydrophilicity, polarity and acidity than those of channel Q.

On the other hand, channel Q is in the form of a pseudo-triangular prism, where two of the three walls forming the triangular prism are surrounded by the π-plane of tris(4-pyridyl)triazine (A), and the third is surrounded by hydrogen atoms on the edge of the π-plane of infinitely stacked tris(4-pyridyl)triazine (A) and 1-hydroxytriphenylene (B$_4$). The hydroxyl group of 1-hydroxytriphenylene (B$_4$) is not oriented toward an inner face of channel Q. The channel P and Q are in a slightly meandering, long and thin form.

X-ray structure analysis revealed that the temperature factor of the atoms constituting the B$_4$ molecule is insignificant and very few disorders in the B$_4$ arrangement in the crystal exist in the stack structure formed from tris(4-pyridyl)triazine (A) as the aromatic compound ligand and 1-hydroxytriphenylene (B$_4$) as the uncoordinating aromatic compound in the polymer complex 4. This result indicates that a structure with extremely high regularity has been constructed in the polymer complex 4.

Further, channels P and Q are different from each other in the diameter of an inscribed circle thereof and in the major and minor axes of an inscribed ellipse thereof (channel P: the major axis of the inscribed ellipse, 8.5 to 10.0 Å, the minor axis of the inscribed ellipse, 6.0 to 8.0 Å, and channel Q: the diameter of the inscribed circle, 4.5 to 7.0 Å).

As described above, the channels P and Q formed in the polymer complex 4 having a single-crystal structure represented by {[(ZnI$_2$)$_3$(A)$_2$(B$_4$)] (nitrobenzene)$_4$(methanol)$_n$}$_z$ (n, z: nonstoichiometric composition)) are different from each other in 3 aspects that are shape, size and atmosphere, and also in that the hydroxy group of 1-hydroxytriphenylene is orientated toward the inner face of channel P only.

X-ray crystal structure analysis indicates that the channel P in the polymer complex 4 includes methanol in the vicinity of the hydroxy group of 1-hydroxytriphenylene and also includes nitrobenzene so as to fill spaces. On the other hand, the channel Q includes nitrobenzene only. Hydrogen of the hydroxy group of 1-hydroxytriphenylene, which is oriented toward the inner face of the channel P, has also been confirmed by X-ray crystal structure analysis (see FIG. 3; FIG. 3B is a magnification of FIG. 3A). It has also been confirmed that hydrogen of the hydroxy group of 1-hydroxytriphenylene is also directed toward methanol.

At this time, the distance between an oxygen atom of the hydroxy group of 1-hydroxytriphenylene, and an oxygen atom of methanol included in channel P, is 2.711 Å, that is, the distance is near and thus a strong hydrogen bonding is estimated to be formed between the methanol and the hydroxy group (see FIG. 4; FIG. 4B is a magnification of FIG. 4A). The (shortest) stacking distance between tris(4-pyridyl)triazine [aromatic compound ligand] and 1-hydroxytriphenylene [uncoordinating aromatic compound] in the stack structure is 3.342 Å that is shorter than the atomic distance (3.5 Å) ascribed to van der Waals' force, thus revealing that the interaction between tris(4-pyridyl)triazine as the aromatic compound ligand and 1-hydroxytriphenylene as the uncoordinating aromatic compound is a (–(interaction, that is, an interaction not attributable to van der Waals' force.

In addition, calculation predicted efficient overlap between the HOMO (highest occupied molecular orbital) of 1-hydroxytriphenylene (B4) and the LUMO (lowest unoccupied molecular orbital) of tris(4-pyridyl)triazine (A) (see FIG. 7). FIG. 7(a) is a view showing (–(stacking between tris(4-pyridyl)triazine (A) and 1-hydroxytriphenylene (B4) in the polymer complex 4, and FIG. 7(b) is a view showing overlap between HOMO and LUMO.

The polymer complex of the present invention represented by the polymer complex 4 described above has, in one molecule thereof, two or more kinds of channel groups different from one another in their affinity for guest components and will, upon contacting with a mixture, permit two or more guest components in the mixture to be included via guest exchange in different channel groups respectively. The guest components incorporated into these channel groups are separated from one another by a rigid main framework of the three-dimensional lattice-like structure. Accordingly, the polymer complex of the present invention enables two or more components that cannot coexist (for example, an acid/base or an oxidizing agent/reducing agent) to be stored in a stable state in one polymer complex or to be transported separately in the polymer complex.

Further, the polymer complex has two or more kinds of channel groups different in their affinity for guest components, so that when the channel space of the channel group in the polymer complex is utilized as a reaction field, the reaction field can be accurately regulated by regulation of characteristics of the channel to realize high-degree of regulation of a chemical reaction. For example, a specific catalyst component can be included in a specific channel group, or different catalyst components can be included in the two or more kinds of channel groups. When the channel space of the channel group is utilized as a reaction field, reaction materials are introduced into a specific channel group where a channel atmosphere unique to the channel group can be utilized to achieve highly selective material exchange.

The polymer complex of the present invention can allow the affinity, for guest components, of the two or more kinds of channel groups formed in one polymer complex to be regulated at will not only by selecting the aromatic compound ligand, the metal ion, and the uncoordinating aromatic compound but also by selecting substituents to be introduced into the uncoordinating aromatic compound. It can thus be expected that the polymer complex is utilized in a variety of applications in various fields, for example, as an additive in a hole-making material used in electrodes of proton-exchange membrane fuel cells or in electrolyte membranes in proton-exchange membrane fuel cells, as well as in technology of removing impurities from methanol that is a fuel for fuel cells of direct methanol charge type.

It is known that in proton-exchange membrane fuel cells, a hole-making material is added for promoting the diffusion of a fuel gas or an oxidant gas, but addition of the hole-making agent causes a problem that water cannot be retained in an electrode (catalyst layer) during operation under low humid conditions so that an electrolyte membrane is dried to reduce electric generation performance. It is estimated that the polymer complex of the present invention has both hydrophilic channels and hydrophobic channels, thus enabling both retention of water in the hydrophilic channels even under low humid conditions and retention of gas dispersibility by the hydrophobic channels. It is also estimated that the polymer complex serves as an additive for an electrolyte membrane of a proton-exchange membrane fuel cell, to allow the electrolyte membrane to retain water in its hydrophilic portion thus making an improvement expectable in electric generation performance.

EXAMPLES

Hereinafter, the present invention is described in more detail by reference to the Examples.
[Production of Polymer Complexes 1 to 7]

4 ml nitrobenzene and 1 ml methanol were placed in a test tube, and 6.3 mg (0.02 mmol) of 2,4,6-tris(4-pyridyl)-1,3,5-triazine was dissolved therein, and each of uncoordinating aromatic compounds (B, B1 to B6) shown in Table 1 was added thereto.

Then, the solution obtained above was used as a bottom layer, and 0.5 ml methanol was added quietly as a buffer as a middle layer thereon. Finally, a solution of 9.6 mg (0.03 mmol) ZnI2 in 0.5 ml methanol was added quietly as a top layer, left at about 23 to 25 (C (room temperature) for about 3 days to give polymer complexes 1 to 6 (Examples 1 to 6) and polymer complex 7 (Comparative Example 1). The uncoordinating aromatic compound used in each of the polymer complexes 1 to 7 and its amount, and the outward appearance of crystals of the polymer complexes 1 to 7, are shown in Table 1. The structural formula of each uncoordinating aromatic compound is shown below.

TABLE 1

| Polymer complex | Uncoordinating aromatic compound | Amount of uncoordinating aromatic compound (mg) | Appearance of crystals |
|---|---|---|---|
| 1 | 1-Nitrotriphenylene ($B_1$) | 21.8 | Pale yellow needle crystals |
| 2 | 1-Aminotriphenylene ($B_2$) | 12.2 | Red needle crystals |
| 3 | 2-Aminotriphenylene ($B_3$) | 12.2 | Dark red needle crystals |
| 4 | 1-Hydroxytriphenylene ($B_4$) | 17.1 | Yellow needle crystals |
| 5 | 2-Hydroxytriphenylene ($B_5$) | 17.1 | Yellow needle crystals |
| 6 | 1-Acetoxytriphenylene ($B_6$) | 15.0 | Yellow needle crystals |
| 7 | Triphenylene (B) | 22.8 | Yellow needle crystals |

[Formula 7]

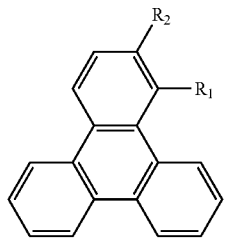

B₁: R₁ = NO₂, R₂ = H
B₂: R₁ = NH₂, R₂ = H
B₃: R₁ = H, R₂ = NH₂
B₄: R₁ = OH, R₂ = H
B₅: R₁ = H, R₂ = OH
B₆: R₁ = OCOCH₃, R₂ = H
B: R₁ = H, R₂ = H (Analysis of Polymer Complex 4)

The resulting polymer complex 4 was analyzed for its X-ray crystal structure. The results are shown below. As described above, FIG. 2 with an axis b in a direction perpendicular to the plane of this figure (crystal 010 plane) shows an interpenetrated structure in the three-dimensional lattice-like structure of the polymer complex 4 along the direction (axis b) in which channels P and Q extend. In FIG. 2, guest components incorporated into channels P and Q are not shown.

Crystal structure analysis was carried out with a Smart 1000 X-ray diffraction instrument (manufactured by Bruker, X-ray source: Mo—K$_\alpha$, temperature: 80K, output: 55 kV, 30 mA) (hereinafter these conditions were used in crystal structure analysis).

The stacking distance between tris(4-pyridyl)triazine and 1-hydroxytriphenylene in the polymer complex 4, and a hydrogen bonding between methanol included in channel P and hydrogen of the hydroxy group of 1-hydroxytriphenylene, areas described above.

<X-ray Crystal Structure Analysis>

Crystallographic data on the polymer complex 4, coordinate information on each atom, etc. are shown in Tables 2 to 5. Table 2 corresponds to FIG. 9; Table 3 (Table 3-1 to Table 3-4) to FIG. 10 to FIG. 13; Table 4 (Table 4-1 to Table 4-4) to FIG. 14 to FIG. 17; and Table 5 (Table 5-1 to Table 5-3) to FIG. 18 to FIG. 20.

(Polymer Complex 3)

Figure 5:
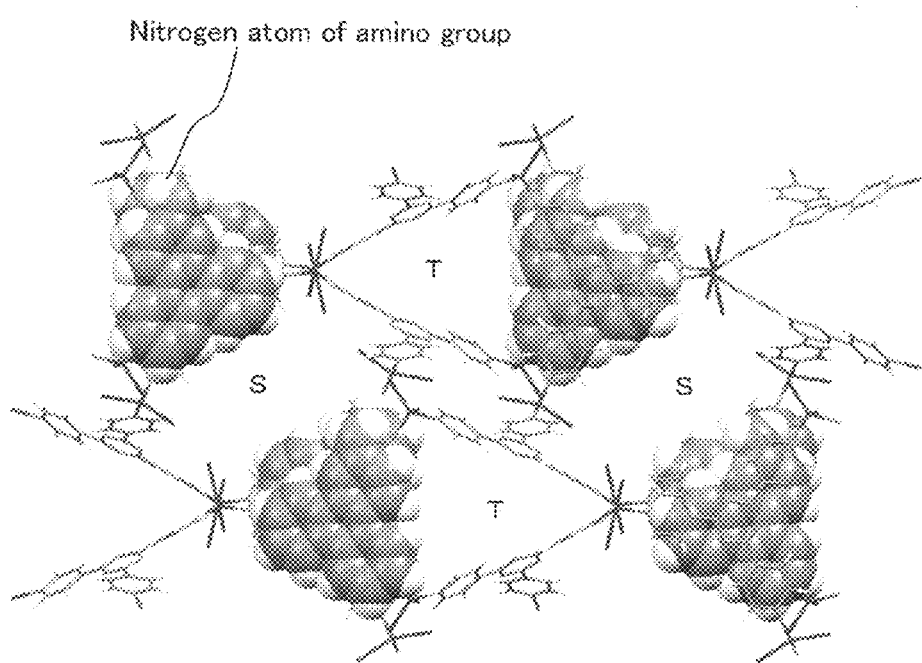
FIG. 5 is a view showing a crystal structure of the polymer complex 4.

The resulting polymer complex 3 was analyzed for its elements and X-ray crystal structure. The results are shown below. FIG. 5 with an axis b in a direction perpendicular to the plane of this figure (crystal 010 plane) shows an interpenetrated structure in the three-dimensional lattice-like structure of the polymer complex 3 along the direction (axis b) in which channels S and T extend. In FIG. 5, guest components incorporated into channels S and T are not shown.

In the polymer complex 3, there are two kinds of channels (S and T) arranged regularly in the 3-dimensional lattice-like structure thereof as shown in FIG. 5. The channels S and T are formed regularly between stack structures having tris(4-pyridyl)triazine (A) and 2-aminotriphenylene (B₃) stacked alternately with one another. The channel S is almost cylindrical and mainly surrounded by hydrogen atoms on the edge of the π-plane of infinitely stacked tris(4-pyridyl)triazine (A) and 2-aminotriphenylene (B₃). The amino group of 2-aminotriphenylene (B₃) is directed to an inner face of channel S to form a part of the inner face of channel S. Accordingly, the channel S is modified with the amino group, thus attaining higher hydrophilicity, polarity and basicity than those of channel T.

On the other hand, channel T is in the form of a pseudo-triangular prism, where two of the three walls forming the triangular prism are surrounded by the π-plane of tris(4-pyridyl)triazine (A), and the third is surrounded by hydrogen atoms on the edge of the π-plane of infinitely stacked tris(4-pyridyl)triazine (A) and 2-aminotriphenylene (B₃). The amino group of 2-aminotriphenylene (B₃) is not oriented toward an inner face of channel T. The channel S and T are in a slightly meandering, long and thin form.

Further, channels S and T are different from each other in the diameter of an inscribed circle thereof and in the major and minor axes of an inscribed ellipse thereof (channel P: the major axis of the inscribed ellipse, 8.5 to 10.0 Å, the minor axis of the inscribed ellipse, 6.0 to 8.0 Å, and channel Q: the diameter of the inscribed circle, 4.5 to 7.0 Å).

As described above, the channels S and T formed in the polymer complex 3 having a single-crystal structure represented by {[(ZnI₂)₃(A)₂(B₃)] (nitrobenzene)₄(methanol)$_n$}$_z$ (n, z: nonstoichiometric composition)) are different from each other in 3 aspects that are shape, size and atmosphere, and also in that the amino group of 2-aminotriphenylene is orientated toward the inner face of channel S only.

<X-ray Crystal Structure Analysis>

Crystallographic data on the polymer complex 3, coordinate information on each atom, etc. are shown in Tables 6 to 9. Table 6 corresponds to FIG. 21; Table 7 (Table 7-1 to Table 7-6) to FIG. 22 to FIG. 27; Table 8 (Table 8-1 to Table 8-6) to FIG. 28 to FIG. 33; and Table 9 (Table 9-1 to Table 9-3) to FIG. 34 to FIG. 36.

In addition, calculation predicted efficient overlap between the HOMO (highest occupied molecular orbital) of 2-aminotriphenylene (B₃) and the LUMO (lowest unoccupied molecular orbital) of tris(4-pyridyl)triazine (A) (see FIG. 8). FIG. 8(*a*) is a view showing π-π stacking between tris(4-pyridyl)triazine (A) and 2-aminotriphenylene (B₃) in the polymer complex 3, and FIG. 8(*b*) is a view showing overlap between HOMO and LUMO.

(Guest Exchange)

The polymer complexes 4, 5 and 7 synthesized as described above were subjected to guest exchange as shown below. That is, each of the polymer complexes was dipped (at 27° C. for 3 days) in a mixture prepared by dissolving 2-propanol in cyclohexane [2-propanol/cyclohexane (volume ratio)=1:39]. The guest components included in the channels in the polymer complexes (hereinafter, the pseudo-triangular channel and cylindrical channel formed in the polymer complexes are referred to channel A and channel B, respectively) are shown in Table 10. Nitrobenzene is a component derived from the crystallization solvent of the polymer complex.

TABLE 10

| Polymer Complex | Channel A | Channel B |
|---|---|---|
| 4 | 2 molecules of cyclohexane | 2 molecules of 2-propanol + 1 molecule of nitrobenzene |
| 5 | 2 molecules of cyclohexane | 3 molecules of 2-propanol |
| 7 | 2 molecules of cyclohexane | 2-molecules of cyclohexane + 1 molecule of nitrobenzene |

As shown in Table 10, the polymer complex 7 using triphenylene having no substituent incorporated cyclohexane into the channels A and B, but did not incorporate 2-propanol, while the polymer complexes 4 and 5 using triphenylene having a hydroxyl group selectively incorporated cyclohexane into the channel A and 2-propanol into the channel B.

FIG. 37 shows the X-ray structure analysis result of the polymer complexes 5 and 7 after the guest exchange experiment (37-A: polymer complex 7, 37-B: polymer complex 5). FIG. 37 is a magnification of the channel B of each polymer complex, where it can be seen that cyclohexane only was incorporated into the polymer complex 7 while 2-propanol was incorporated into the polymer complex 5.

This result is considered to suggest that the alcohol molecule (2-propanol) is incorporated into the channel B by hydrogen bonding to a hydroxyl group in the channel B. That is, it is revealed that the ability to absorb guest molecules can be regulated and extended by introduction of the functional group into the channel.

Comparison between the polymer complexes 4 and 5 revealed that because they are different in the component incorporated into the channel B, the affinity of the channel B for guest components, that is, the ability thereof to recognize guest components, varies significantly depending on the position of the substituent introduced into triphenylene as the uncoordinating aromatic compound. That is, the affinity of the channel for guest components can be accurately regulated not only by the type of a substituent on the uncoordinating aromatic compound but also by regulation of the position of the substituent thereon.

From the above result, it was suggested that the polymer complexes 4 and 5 have an ability to incorporate the alcohol molecule selectively and are available in technology of selecting and separating alcohol. Separation of alcohol by utilizing the inclusion ability of the polymer complex of the present invention to include guest components does not require energy and can thus realize the separation, with high energy efficiency, of alcohol noticeable as fuel.

The invention claimed is:

1. A polymer complex comprising an aromatic compound having two or more coordinating sites as a ligand, a metal ion as a central metal, and an uncoordinating aromatic compound, wherein:
the polymer complex has a three-dimensional structure containing a stack structure comprising the uncoordinating aromatic compound intercalated between aromatic compound ligands in a three-dimensional coordination network formed by coordinating the aromatic compound ligands to the central metal ion,
the three-dimensional structure is provided with two or more kinds of channel groups each composed of channels identical with one another and having inherent affinity for guest components,
wherein the central metal is at least one selected from copper, nickel, cobalt, iron and silver;
wherein the aromatic ring of the uncoordinating aromatic compound is selected from the following formulae 5(c), 5(d) and 5(f)-5(i)

5 (c)
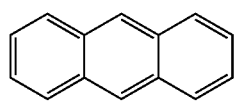

-continued 5 (d)
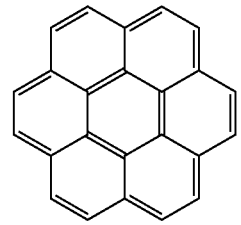

5 (f)
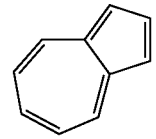

5 (g)
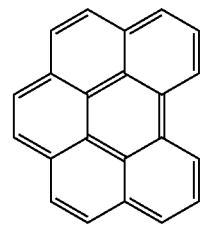

5 (h)
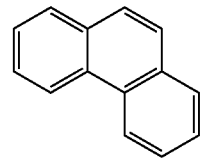

5 (i)
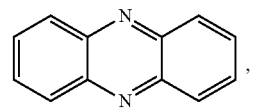

the uncoordinating aromatic compound has at least one substituent A at a specific position on the aromatic ring thereof, selected from —W—OH, —W—NH$_2$, —W—NO$_2$, —W—CH$_3$, —W—OCOCH$_3$, an alkyl ether chain, an alkylthio ether chain, an alkylene glycol chain, and a peptide chain, wherein W represents a divalent organic group or a single bond, and
the uncoordinating aromatic compound is arranged regularly such that the substituent A is directed to the inside of a specific channel group B out of the two or more kinds of channel groups.

2. The polymer complex according to claim 1, which can selectively incorporate, release and/or transport guest components.

3. The polymer complex according to claim 1, wherein the three-dimensional coordination network is a complexed three-dimensional coordination network comprising two or more independent three-dimensional coordination networks complexed with one another.

4. The polymer complex according to claim 3, wherein the complexed three-dimensional coordination network is an interpenetrated structure.

5. The polymer complex according to claim 1, wherein two channel groups selected arbitrarily from the two or more kinds of channel groups are different from each other in at least one factor selected from the size of a channel, the shape of a channel and the atmosphere in a channel in comparison therebetween.

6. The polymer complex according to claim 1, wherein the diameter of an inscribed circle of a channel contained in a channel group selected from the two or more kinds of channel groups is 2 to 70 Å on a face parallel to a crystal plane most perpendicular to the direction in which the channel extends.

7. The polymer complex according to claim 1, wherein the major axis of an inscribed ellipse of a channel contained in a channel group selected from the two or more kinds of channel groups is 5 to 70 Å, and the minor axis of the inscribed ellipse is 2 to 50 Å, on a face parallel to a crystal plane most perpendicular to the direction in which the channel extends.

8. The polymer complex according to claim 1, wherein the aromatic compound ligand is an aromatic compound represented by the following formula (1):

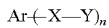

wherein Ar is a structure having an aromatic ring, X is a divalent organic group or a single bond through which Ar and Y are directly bound to each other. Y is a coordinating atom or a coordinating atom-containing atomic group, n is a number of 3 to 6, and a plurality of Xs contained in one molecule may be different from one another, and a plurality of Ys may be different from one another.

9. The polymer complex according to claim 1, wherein the substituent A can exhibit an intramolecular interaction higher than van der Waals' force in the polymer complex.

10. The polymer complex according to claim 1, wherein the HOMO (highest occupied molecular orbital) of the uncoordinating aromatic compound and the LUMO (lowest unoccupied molecular orbital) of the aromatic compound ligand have an overlapping of orbital shape in the stack structure in the three-dimensional coordination network, thereby stabilizing the stack structure.

11. The polymer complex according to claim 1, wherein the substituent A is at least one functional group selected from —W—OH, —W—NH$_2$, —W—CH$_3$, and an alkyl ether chain, wherein W represents a divalent organic group or a single bond.

12. The polymer complex according to claim 1, wherein the substituent A is an atomic group having 3 or less atoms in total excluding hydrogen atoms.

13. The polymer complex according to claim 1, wherein the diameter of an inscribed circle of a channel contained in a channel group selected from the two or more kinds of channel groups is 4.5 to 7.0 Å on a face parallel to a crystal plane most perpendicular to the direction in which the channel extends.

14. The polymer complex according to claim 1, wherein the major axis of an inscribed ellipse of a channel contained in a channel group selected from the two or more kinds of channel groups is 8.5 to 10.0 Å, and the minor axis of the inscribed ellipse is 6.0 to 8.0 Å, on a face parallel to a crystal plane most perpendicular to the direction in which the channel extends.

15. The polymer complex according to claim 1, wherein the substituent A is at least one functional group selected from —W—OH, —W—NH$_2$, and —W—CH$_3$, wherein W represents a divalent organic group or a single bond.

16. The polymer complex according to claim 8, wherein the aromatic compound represented by the formula (1) as the aromatic compound ligand is tris(4-pyridyl)triazine.

* * * * *